US012629011B2

(12) United States Patent
Hayashi et al.

(10) Patent No.: US 12,629,011 B2
(45) Date of Patent: May 19, 2026

(54) LIGHT SOURCE DEVICE AND ENDOSCOPE SYSTEM

(71) Applicant: HOYA CORPORATION, Tokyo (JP)

(72) Inventors: Yoshihiro Hayashi, Tokyo (JP); Yoshiyuki Niijima, Tokyo (JP); Yukari Akino, Tokyo (JP); Shinya Shimotashiro, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 407 days.

(21) Appl. No.: 18/029,738

(22) PCT Filed: Nov. 4, 2021

(86) PCT No.: PCT/JP2021/040547

§ 371 (c)(1),
(2) Date: Mar. 31, 2023

(87) PCT Pub. No.: WO2022/097671

PCT Pub. Date: May 12, 2022

(65) Prior Publication Data

US 2023/0363630 A1 Nov. 16, 2023

(30) Foreign Application Priority Data

Nov. 9, 2020 (JP) ................................ 2020-186299

(51) Int. Cl.
*A61B 1/06* (2006.01)
*A61B 1/00* (2006.01)

(52) U.S. Cl.
CPC ........ *A61B 1/0684* (2013.01); *A61B 1/00009* (2013.01); *A61B 1/0638* (2013.01);
(Continued)

(58) Field of Classification Search
CPC . A61B 1/0684; A61B 1/00009; A61B 1/0638; A61B 1/0655; A61B 1/00045;
(Continued)

(56) References Cited

U.S. PATENT DOCUMENTS 8,785,833 B2 7/2014 Yabe et al.
10,447,939 B2 * 10/2019 Kobayashi ............ A61B 1/045
(Continued)

FOREIGN PATENT DOCUMENTS

CN 103841881 A 6/2014
CN 108778090 A 11/2018
(Continued)

OTHER PUBLICATIONS

Extended European search report issued in EPO Patent Application No. 21889224.8, dated Nov. 12, 2024.
(Continued)

*Primary Examiner* — Sonji N Johnson
(74) *Attorney, Agent, or Firm* — Greenblum & Bernstein, P.L.C.

(57) ABSTRACT

A light source device according to the present disclosure is a light source device that generates illumination light with which an object is to be irradiated, the light source device including: a plurality of semiconductor light emitting elements configured to emit light having different wavelength bands; and a control unit configured to control a light emission profile of the plurality of semiconductor light emitting elements and drive the plurality of semiconductor light emitting elements, in which the control unit extends the light emission profile in a first direction that is a direction opposite to a direction in which time progresses in a case of increasing an exposure level and shortens the light emission profile from a second direction that is the direction in which time progresses in a case of decreasing the exposure level.

7 Claims, 13 Drawing Sheets

(52) U.S. Cl.
CPC ........ *A61B 1/0655* (2022.02); *A61B 1/00045* (2013.01); *A61B 1/0676* (2013.01)

(58) Field of Classification Search
CPC . A61B 1/0676; A61B 1/00006; A61B 1/0669; A61B 1/07; G02B 19/0014; G02B 19/0066; G02B 23/2461; G02B 27/0905; G02B 27/0961
See application file for complete search history.

(56) References Cited

U.S. PATENT DOCUMENTS

| | | | |
|---|---|---|---|
| 11,607,110 | B2 | 3/2023 | Hayashi |
| 2014/0014820 | A1 | 1/2014 | Yabe et al. |
| 2014/0203170 | A1 | 7/2014 | Ono et al. |
| 2017/0095297 | A1 | 4/2017 | Richmond et al. |
| 2019/0008372 | A1 | 1/2019 | Tanaka et al. |
| 2019/0150790 | A1 | 5/2019 | Shimotashiro et al. |
| 2020/0178781 | A1 | 6/2020 | Tabata et al. |
| 2020/0229688 | A1 | 7/2020 | Yoshino et al. |
| 2020/0297184 | A1 | 9/2020 | Kono |
| 2021/0113075 | A1 | 4/2021 | Ito et al. |
| 2023/0089085 | A1 | 3/2023 | Niijima et al. |
| 2025/0275674 | A1* | 9/2025 | Shimomura ........... A61B 1/045 |

FOREIGN PATENT DOCUMENTS

| | | | |
|---|---|---|---|
| JP | 5379932 | B1 | 10/2013 |
| JP | 2013/175908 | A1 | 11/2013 |
| JP | 2017-510348 | A | 4/2017 |
| JP | 6239220 | B1 | 11/2017 |
| JP | 2018-182580 | A | 11/2018 |
| JP | 2020-151090 | A | 9/2020 |
| WO | 2013/157368 | A1 | 10/2013 |
| WO | 2020/012563 | A1 | 1/2020 |

OTHER PUBLICATIONS

U.S. Appl. No. 18/024,578 to Yoshihiro Hayashi et al., filed Mar. 3, 2023.

International Search Report issued in International Bureau of WIPO Patent Application No. PCT/JP2021/040547, dated Jan. 11, 2022, along with an English translation thereof.

Notice of Reasons for Refusal issued in Japan Patent Application No. 2020-186299, dated Apr. 2, 2024, along with an English translation thereof.

First Office Action issued in Chinese Patent Application No. 202180062409.4, dated Mar. 20, 2026, together with an English-language translation.

* cited by examiner

CONFIGURATION EXAMPLE OF LIGHT SOURCE USING LEDS HAVING DIFFERENT LIGHT DISTRIBUTION

EXAMPLE OF EMITTED LIGHT AMOUNT/ CURRENT RATIO OF EACH LED

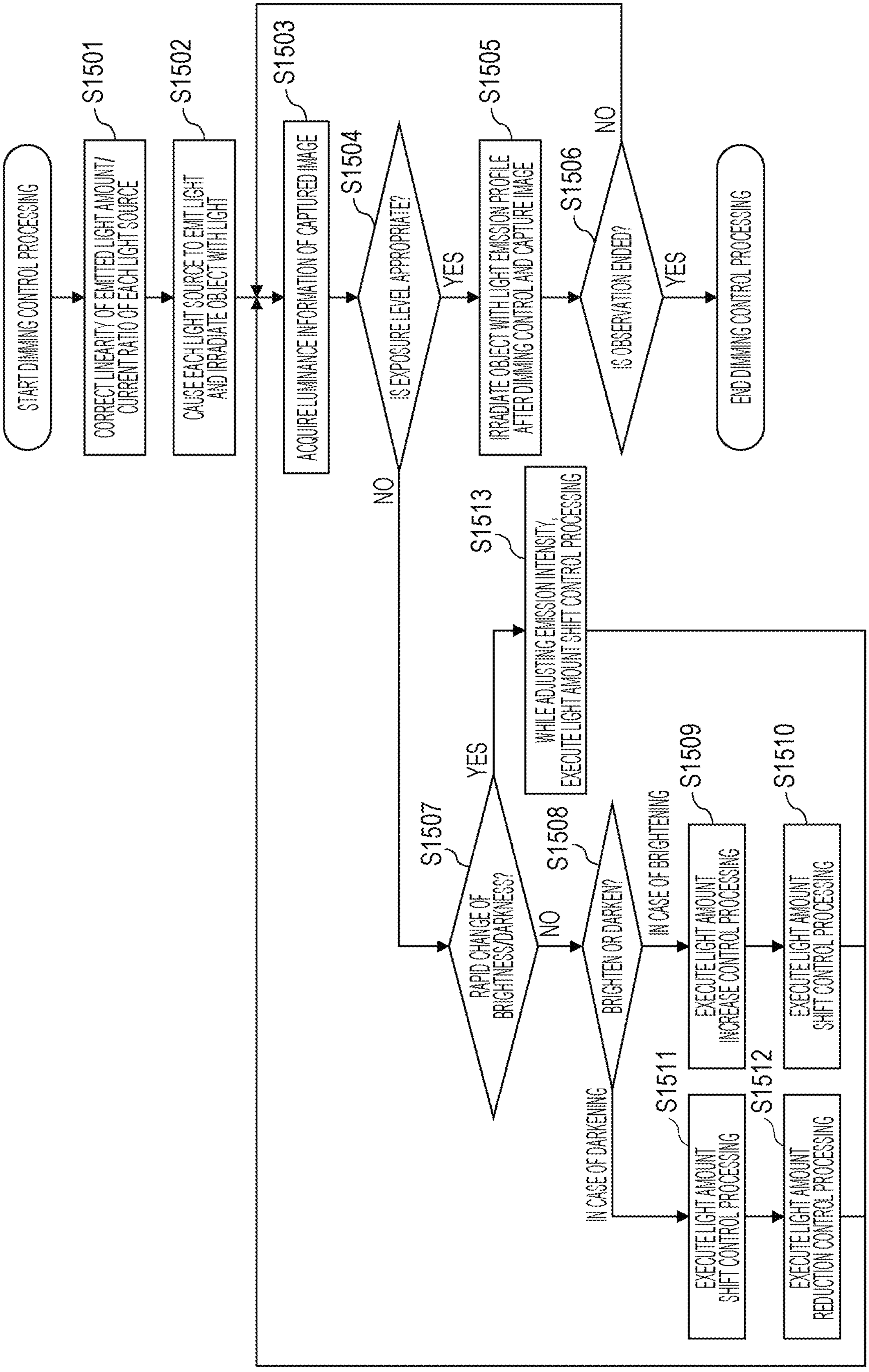

*FIG. 15*

START DIMMING CONTROL PROCESSING

S1501
CORRECT LINEARITY OF EMITTED LIGHT AMOUNT/ CURRENT RATIO OF EACH LIGHT SOURCE

S1502
CAUSE EACH LIGHT SOURCE TO EMIT LIGHT AND IRRADIATE OBJECT WITH LIGHT

S1503
ACQUIRE LUMINANCE INFORMATION OF CAPTURED IMAGE

S1504
IS EXPOSURE LEVEL APPROPRIATE?
YES / NO

S1505
IRRADIATE OBJECT WITH LIGHT EMISSION PROFILE AFTER DIMMING CONTROL AND CAPTURE IMAGE

S1506
IS OBSERVATION ENDED?
NO / YES

END DIMMING CONTROL PROCESSING

S1507
RAPID CHANGE OF BRIGHTNESS/DARKNESS?
YES / NO

S1513
WHILE ADJUSTING EMISSION INTENSITY, EXECUTE LIGHT AMOUNT SHIFT CONTROL PROCESSING

S1508
BRIGHTEN OR DARKEN?
IN CASE OF BRIGHTENING / IN CASE OF DARKENING

S1509
EXECUTE LIGHT AMOUNT INCREASE CONTROL PROCESSING

S1510
EXECUTE LIGHT AMOUNT SHIFT CONTROL PROCESSING

S1511
EXECUTE LIGHT AMOUNT SHIFT CONTROL PROCESSING

S1512
EXECUTE LIGHT AMOUNT REDUCTION CONTROL PROCESSING

LIGHT SOURCE DEVICE AND ENDOSCOPE SYSTEM

TECHNICAL FIELD

The present disclosure relates to a light source device and an endoscope system.

BACKGROUND ART

In a normal endoscope device equipped with a rolling shutter type image sensor, a light source is turned off in an effective pixel readout period (rolling shutter period) of the image sensor, and the light source is turned on in other periods (pseudo global exposure period) (pulse light emission control is performed), thereby executing pseudo global exposure and avoiding occurrence of an undesirable phenomenon caused by the rolling shutter, for example, distortion or artifacts.

On the other hand, if the light source is completely turned off during the rolling shutter period, a light amount becomes insufficient depending on an object (observation target site), and a favorable image cannot be acquired. For example, Patent Literatures 1 to 3, and the like, disclose light source control in which part of the rolling shutter period is included in a pulse light emission period in order to solve the insufficient light amount.

CITATION LIST

Patent Literature

Patent Literature 1: JP 2018-182580 A
Patent Literature 2: JP 5379932 B1
Patent Literature 3: JP 6239220 B1

SUMMARY OF INVENTION

Technical Problem

However, if the light source control as described in Patent Literatures 1 to 3 is executed, brightness unevenness, lateral stripes, and the like, of a screen occur due to an exposure period difference for each line in adjacent frames. Then, there is a problem that the brightness unevenness and the lateral stripes move up and down on a display screen due to change in the pulse light emission period for each frame and become offensive. In addition, in a case where offset light emission is performed during the rolling shutter period in order to solve the insufficient light amount, if the offset light emission becomes strong to some extent, an unnatural image in which a long-time exposure image and a high-speed exposure image are doubly exposed is generated.

The present disclosure has been made in view of such a situation and proposes a technique of securing a sufficient light amount while avoiding occurrence of distortion and artifacts caused by a rolling shutter and making brightness unevenness and lateral stripes less noticeable even if change in a pulse light emission period extends over a rolling shutter period.

Solution to Problem

In order to solve the above problem, the present embodiment proposes a light source device that generates illumination light with which an object is to be irradiated, the light source device including: a plurality of semiconductor light emitting elements configured to emit light having different wavelength bands; and a control unit configured to control a light emission profile of the plurality of semiconductor light emitting elements and drive the plurality of semiconductor light emitting elements, in which the control unit extends the light emission profile in a first direction that is a direction opposite to a direction in which time progresses in a case of increasing an exposure level and shortens the light emission profile from a second direction that is the direction in which time progresses in a case of decreasing the exposure level.

In addition, the present embodiment proposes an endoscope system that inserts an endoscope into an observation target and acquires an image of an object, the endoscope system including: a plurality of semiconductor light emitting elements configured to emit light having different wavelength bands; an image sensor configured to irradiate the object with illumination light and detect reflected light from the object to generate an image signal; a processor configured to process the image signal to generate the image of the object and display the image on a monitor; a main control unit configured to generate a control signal for controlling a light emission profile of the plurality of semiconductor light emitting elements on the basis of the image signal; and a light source control unit configured to receive the control signal from the main control unit and drive the plurality of semiconductor light emitting elements with a drive signal according to the light emission profile, in which the light emission profile defines (i-1) a period during which illumination light is emitted in at least part of a pseudo global exposure period of the image sensor that captures the image of the object or (i-2) a pulse light emission period indicating a period during which illumination light is emitted in at least part of the pseudo global exposure period of the image sensor and a rolling shutter period, and (ii) pulse light emission intensity indicating intensity of the illumination light in the pulse light emission period, and the main control unit extends the light emission profile in a first direction that is a direction opposite to a direction in which time progresses in a case of increasing an exposure level and shortens the light emission profile from a second direction that is the direction in which time progresses in a case of decreasing the exposure level.

Further features related to the present disclosure will become apparent from the description of the present specification and the accompanying drawings. The present disclosure is achieved and implemented by elements and combinations of various elements and by modes of the following detailed description and the appended claims.

It is to be understood that the description in this specification is merely exemplary and is not intended to limit the scope of the claims or the application in any significance.

Advantageous Effects of Invention

According to the present disclosure, it is possible to secure a sufficient light amount while avoiding occurrence of distortion and artifacts caused by a rolling shutter and to make brightness unevenness and lateral stripes less noticeable even if change in a pulse light emission period extends over a rolling shutter period.

BRIEF DESCRIPTION OF DRAWINGS

FIG. 15 is a flowchart for explaining dimming control processing according to the present embodiment.

DESCRIPTION OF EMBODIMENTS

Hereinafter, embodiments of the present disclosure will be described with reference to the drawings. In the following, an endoscope system will be described as an embodiment of the present disclosure.

An observation target site in the endoscope system is, for example, respiratory organs or digestive organs. Examples of the respiratory organs include the lungs, the bronchus, the ears, the nose, and the throat. Examples of the digestive organs include the large intestine, the small intestine, the stomach, the esophagus, the duodenum, the uterus, and the bladder. In a case of observing the target sites as described above, it is more effective to utilize an image in which a specific biological structure is emphasized.

<Configuration of Endoscope System>

Figure 1:
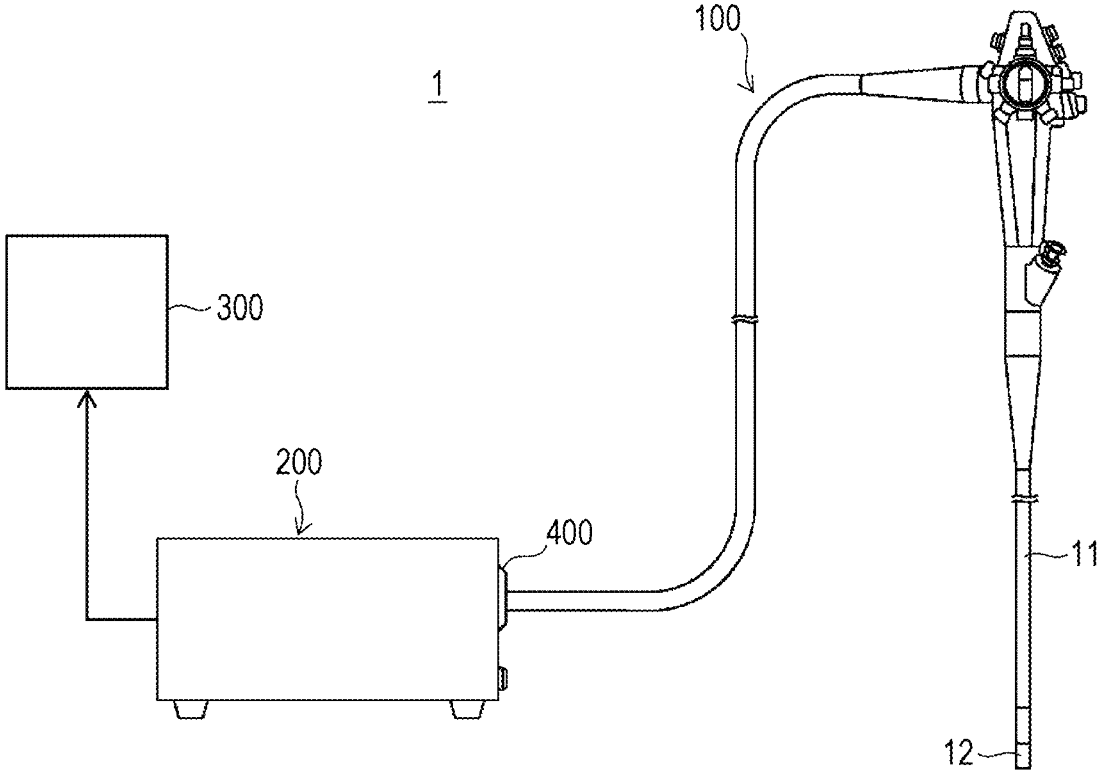
FIG. 1 is a view illustrating an overall external appearance example of an endoscope system according to the present embodiment.
Figure 2:
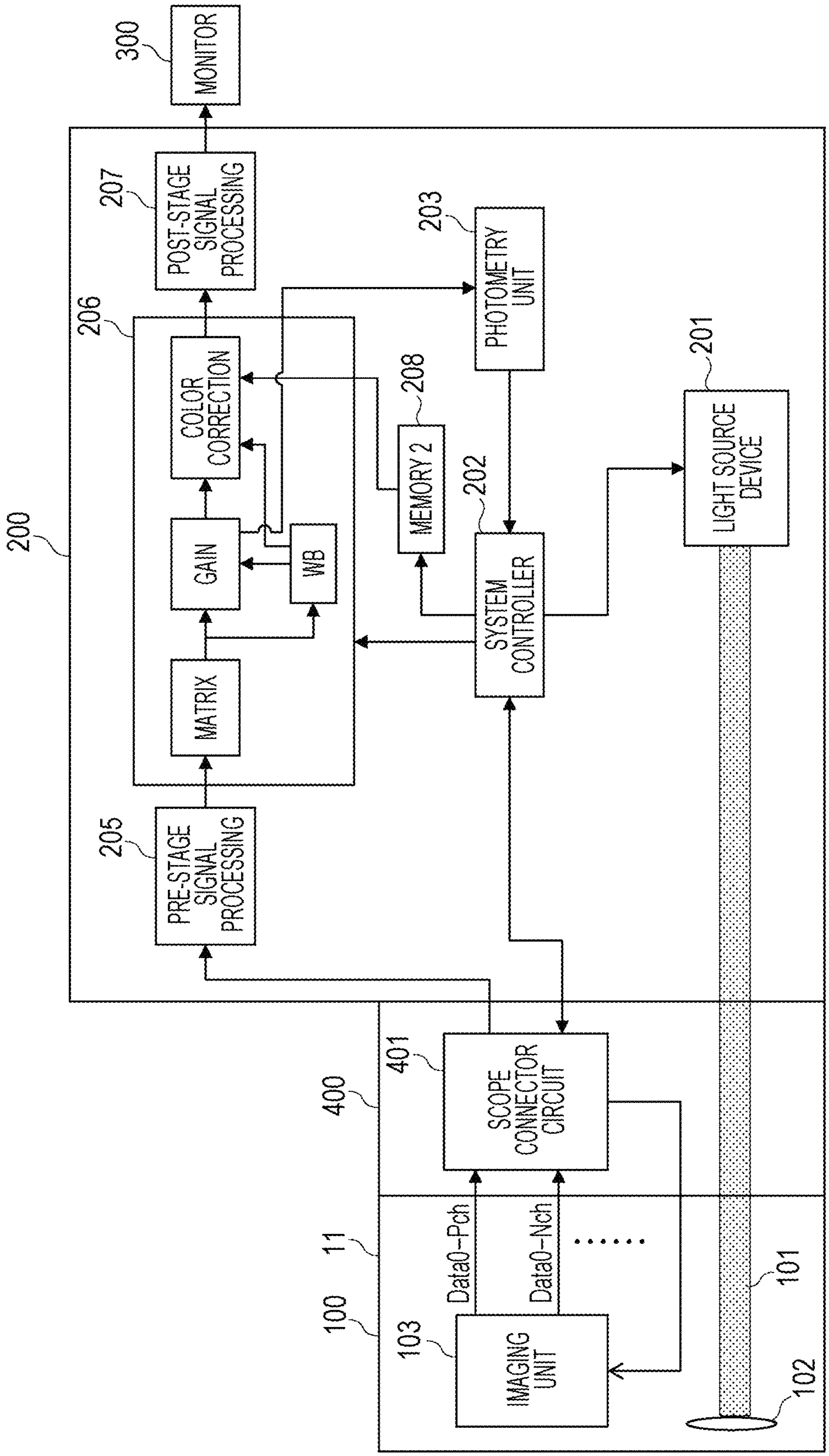
FIG. 2 is a view illustrating a schematic internal configuration example of the endoscope system according to the present embodiment.

FIG. 1 is a view illustrating an example of an overall external appearance of an endoscope system of the present embodiment, and FIG. 2 is a view illustrating a schematic internal configuration example of the endoscope system of the present embodiment. An endoscope system 1 includes an endoscope device (electronic scope) 100, a processor 200, and a monitor 300. Note that a scope connector (which may hereinafter be simply referred to as a "connector") 400 including a connector circuit according to a feature of the present embodiment is provided at a processor-side end portion of the endoscope device 100.

The endoscope device 100 includes an elongated tubular insertion portion 11 to be inserted into a subject. The endoscope device 100 includes a light carrying bundle (LCB) 101 for guiding irradiation light from a light source device 201 to be described later, a light distribution lens 102 provided at an emission end of the LCB 101, an imaging unit 103 that receives return light from an irradiated portion (observation site) via an objective lens (not illustrated), a driver signal processing circuit 105 that drives the imaging unit 103, and a first memory 106.

The irradiation light from the light source device 201 enters the LCB 101 and propagates by repeating total reflection in the LCB 101. The irradiation light (illumination light) propagating in the LCB 101 is emitted from the emission end of the LCB 101 disposed in a distal end portion 12 of the insertion portion 11 and irradiates the observation site through the light distribution lens 102. The return light from the irradiated portion forms an optical image by each pixel on a light receiving surface of the imaging unit 103 via the objective lens.

The imaging unit 103 is disposed in the distal end portion 12 of the insertion portion 11 and can use a complementary metal oxide semiconductor (CMOS) image sensor which is a rolling shutter type image sensor. The imaging unit 103 accumulates optical images (return light from a living tissue) formed by each pixel on the light receiving surface, as charges corresponding to a light amount and generates and outputs image signals of R, G, and B. Note that the imaging unit 103 is not limited to the CMOS image sensor and may be replaced with another type of imaging device as long as it is based on the rolling shutter scheme. A signal output from the imaging unit 103 is processed by a scope connector circuit 401 provided in the scope connector 400 as described later.

The processor 200 is a device that integrally includes a signal processing device that processes a signal from the endoscope device 100 and a light source device that irradiates, via the endoscope device 100, a body cavity where natural light cannot reach. In another embodiment, the signal processing device and the light source device may be provided separately. The processor 200 includes a light source device 201, a system controller 202, a photometry unit 203, a pre-stage signal processing circuit 205, a color conversion circuit 206, a post-stage signal processing circuit 207, and a second memory 208.

The processor 200 may include an operation panel (not illustrated). There are various forms in a configuration of the operation panel. Examples of a specific configuration of the operation panel include a hardware key for each function mounted on a front surface of the processor 200, a touch panel type graphical user interface (GUI), a combination of the hardware key and the GUI, and the like. An operator (surgeon) can perform mode switching operation described later with the operation panel.

The photometry unit 203 acquires luminance information of an image signal obtained by imaging from a gain circuit included in the color conversion circuit 206, compares the acquired luminance information with a predetermined appropriate luminance value (for example, information of the appropriate luminance value can be stored in advance in an internal memory (not illustrated) of the photometry unit 203) and notifies the system controller 202 of a comparison result (whether a current luminance value is appropriate, higher or lower).

The system controller 202 executes various programs stored in a memory (not illustrated) and integrally controls the entire endoscope system 1. The system controller 202 controls operation and timings of various circuits in the processor 200 by using a control signal so as to perform processing suitable for the endoscope device 100 connected to the processor 200. Further, the system controller 202 may be connected to the above-described operation panel.

In addition, the system controller 202 receives the comparison result with the appropriate luminance value from the photometry unit 203, determines whether to maintain current exposure (exposure), whether to increase the exposure (including a level value to increase), or whether to decrease the exposure (including a level value to decrease) and outputs the comparison result to the light source device 201 as an exposure control signal.

The system controller 202 changes each operation of the endoscope system 1 and parameters for each operation in accordance with an operator's instruction input from the operation panel. For example, when the operator selects an observation mode with the operation panel (mode switching operation), the system controller 202 outputs a mode selection signal for causing the light source corresponding to the observation mode to emit light to the light source device 201. As described later, as the light source device 201, for example, a plurality of light emitting diodes (LEDs) that emit light of different wavelength bands can be used (see FIG. 3). When the operator selects an observation mode (for example, a normal observation mode, a special light observation mode, a SatO2 mode, and the like) by operating a mode selection switch provided in the processor 200, for example, the system controller 202 generates a mode selection signal corresponding to the selected mode and supplies the mode selection signal to the light source control unit 2016 of the light source device 201 (see FIG. 3). Based on the mode selection signal, the light source control unit 2016 determines a combination of LEDs to be emitted and their intensity and light amounts (for example, a combination, and the like, of light emitting LEDs corresponding to the mode selection signal are stored in advance in an internal memory (not illustrated)) and outputs a necessary LED control signal from the LEDs 2011 to 2015. When each of the LEDs 2011 to 2015 emits light of each wavelength band based on the LED control signal supplied from the light source control unit 2016, the emitted light is synthesized by a cross prism to generate irradiation light (synthesized light).

The endoscope device 100 and the processor 200 may perform data communication using a wired electric communication scheme or an optical wireless communication scheme.

As illustrated in FIG. 2, the endoscope device 100 and the processor 200 are connected via the scope connector 400. The connector 400 includes an LCB constituting part of the LCB 101 continuing from the processor 200 to the endoscope device 100 and a scope connector circuit 401. Further, the scope connector circuit 401 is provided in the scope connector 400 in the present embodiment, but is not necessarily provided in the scope connector 400. For example, a circuit corresponding to the scope connector circuit 401 may be provided in a connector unit on the processor 200 side or inside the processor 200.

<Internal Configuration Example of Light Source Device 201>

Figure 3:
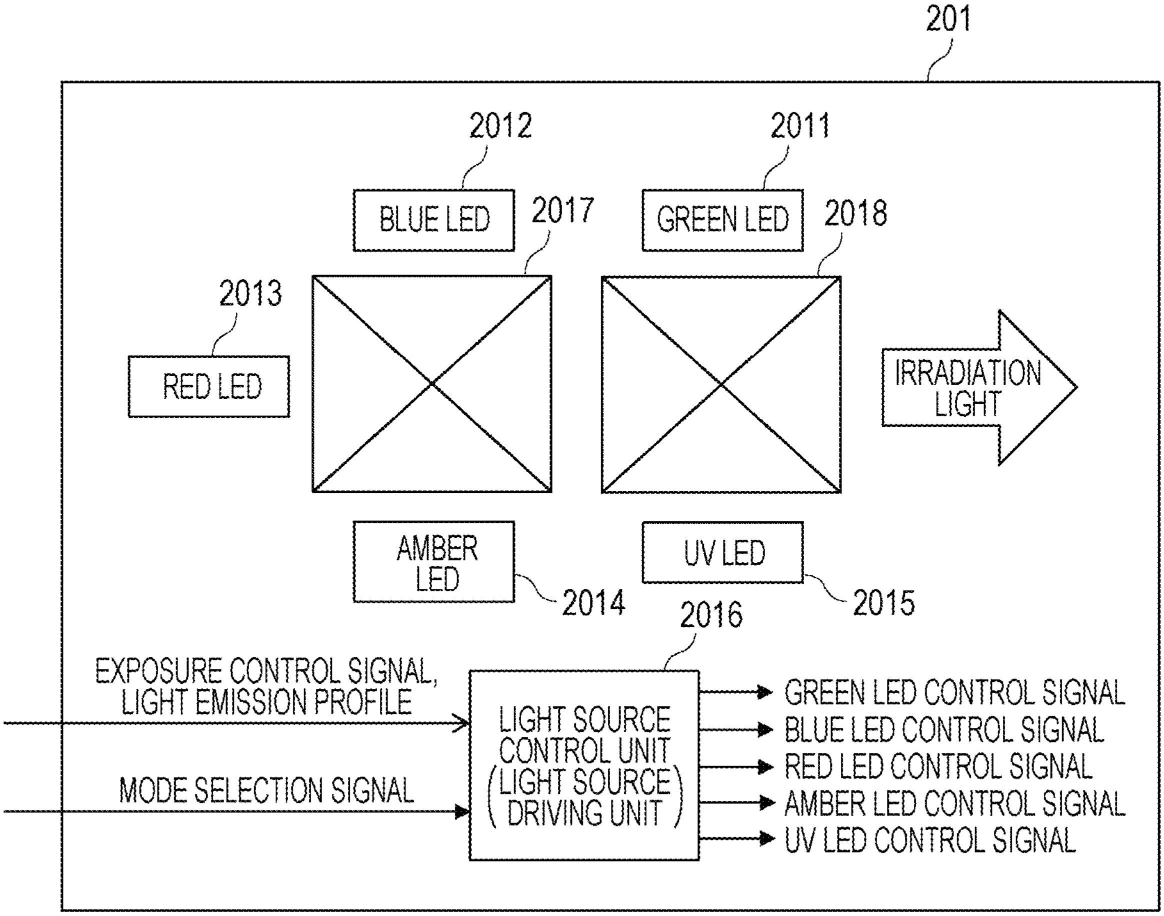
FIG. 3 is a view illustrating an internal configuration example of a light source device 201 provided inside a processor 200.

FIG. 3 is a view illustrating an internal configuration example of the light source device 201 provided inside the processor 200, for example.

The light source device 201 includes a green LED 2011 that emits green light, a blue LED 2012 that emits blue light, a red LED 2013 that emits red light, an amber LED 2014 that emits amber light, a UV LED 2015 that emits UV light, a light source control unit 2016 that controls light emission of the LEDs 2011 to 2015, and cross prisms 2017 and 2018.

If the light source control unit 2016 receives the exposure control signal from the system controller 202, the light source control unit 2016 changes the light emission profile of each LED and performs exposure adjustment (light amount adjustment) by controlling a light emission period and an applied current value of each LED that is currently emitting light (a combination of LEDs to be emitted is determined depending on the observation mode) (see FIG. 12 described later). For example, after changing the light emission profile by one step, the light source control unit 2016 determines whether to change the light emission profile again and perform exposure adjustment on the basis of the exposure control signal determined by a photometry result (comparison result with the appropriate luminance value) by the photometry unit 203.

In addition, the light source control unit 2016 determines a combination of LEDs to emit light on the basis of the mode selection signal indicating the observation mode selected by the operator. In a light emission start stage, the light source control unit 2016 controls light emission of each LED on the basis of, for example, a predetermined light emission profile (a default light emission period and a drive current value), and thereafter, performs exposure adjustment as described above.

<Each LED Light Source>

Figure 4:
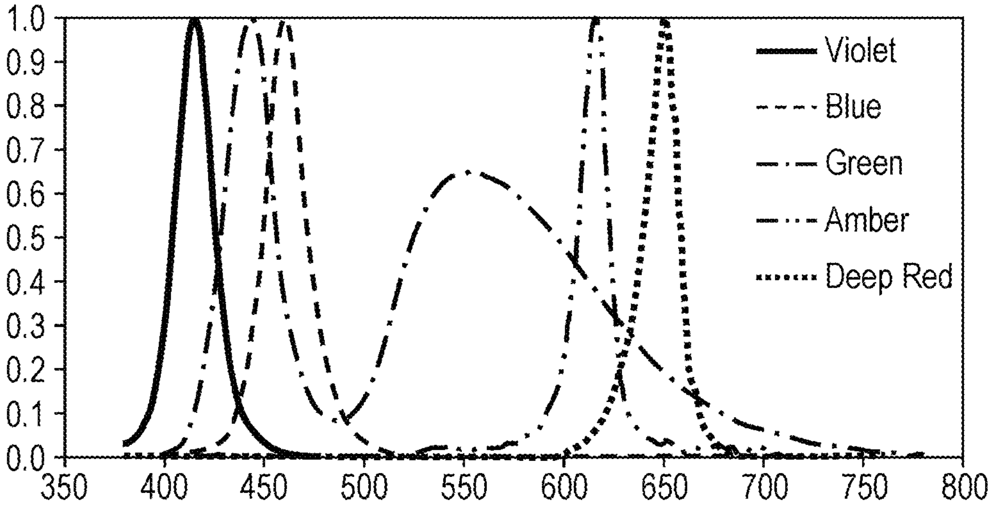
FIG. 4 is a view illustrating spectra (wavelength characteristics) of LEDs 2011 to 2015.

FIG. 4 is a view illustrating spectra (wavelength characteristics) of the LEDs 2011 to 2015. Further FIG. 5 is a view illustrating characteristics of illumination light (light illuminating the observation site) generated by transmitting the respective LEDs through the cross prisms 2017 and 2018.

A transmission wavelength band of the green LED 2011 is 540 nm to 575 nm, a peak wavelength is 550 nm, and a half-value width is 30 nm. A phosphor is mounted on the green LED 2011, and the phosphor emits light in a transmission wavelength range of about 400 nm to 780 nm as illustrated in FIG. 4. In other words, although white light is substantially emitted by the green LED and the phosphor, this white light is an intermediate product, and as described later, the transmission wavelength band is narrowed by the cross prism 2018, and the observation site is irradiated with green light. A transmission wavelength band of the blue LED 2012 is 460 nm to 490 nm, a peak wavelength is 456 nm, and a half-value width is 21 nm. A transmission wavelength band of the red LED 2013 is 630 nm to 1000 nm, a peak wavelength is 650 nm, and a half-value width is 20 nm. A transmission wavelength band of the amber LED 2014 is 600 nm to 615 nm, a peak wavelength is 613 nm, and a half-value width is 19 nm. A transmission wavelength band of the UV LED 2015 is 385 nm to 425 nm, a peak wavelength is 405 nm, and a half-value width is 14 nm.

Figure 5:
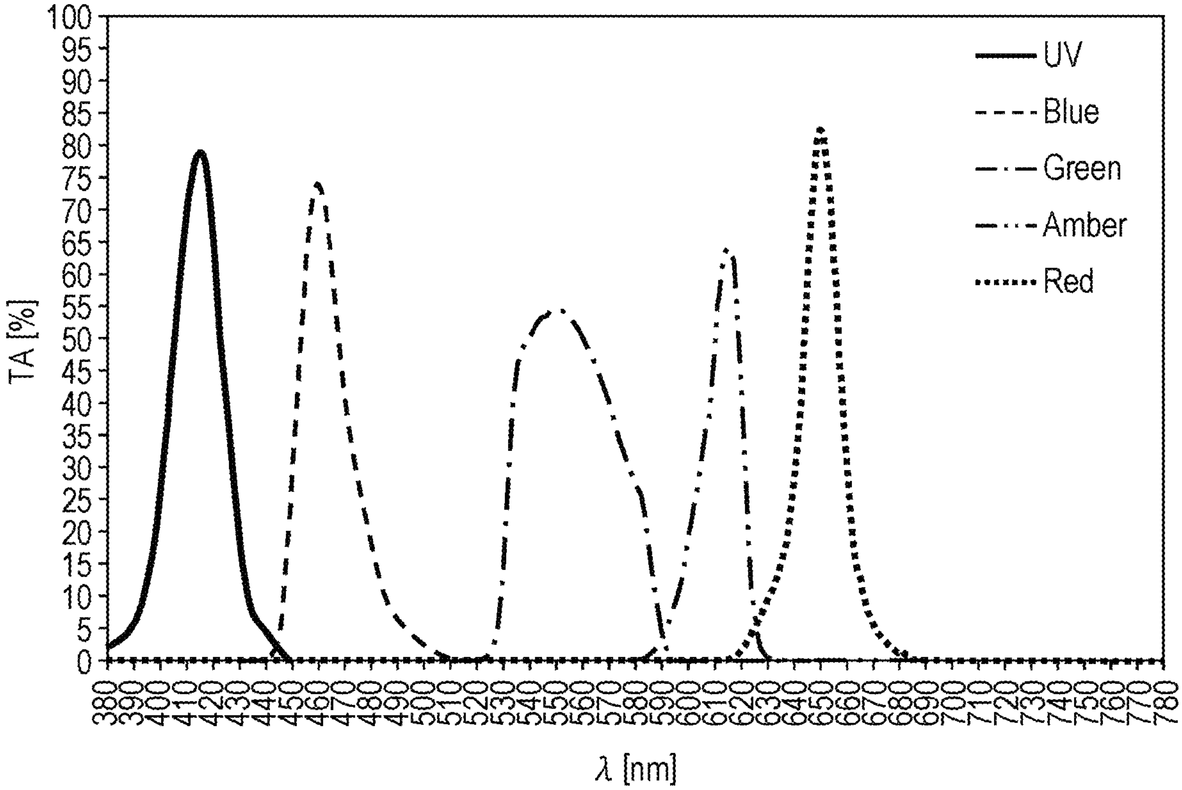
FIG. 5 is a view illustrating characteristics of illumination light (light illuminating an observation site) generated by transmitting each LED through cross prisms 2017 and 2018.

If light (white light, blue light, red light, amber light, UV light as intermediate product) generated from the LEDs 2011 to 2015 including the green LED 2011 on which the phosphor is mounted is transmitted through the cross prisms 2017 and 2018, the observation site is irradiated with light having characteristics illustrated in FIG. 5. Specifically, a transmission wavelength band of the white light generated from the green LED 2011+the phosphor is limited by the cross prism 2018, and the white light becomes green light of 520 nm to 595 nm. The blue light emitted from the blue LED 2012 becomes blue light of 440 nm to 500 nm by the cross prisms 2017 and 2018. In addition, the red light emitted from the red LED 2013 becomes red light of 620 nm to 630 nm by the cross prisms 2017 and 2018. The amber light emitted from the amber LED 2014 becomes amber light of 580 nm to 630 nm by the cross prisms 2017 and 2018. Further, the UV light emitted from the UV LED 2015 becomes UV light of 380 nm to 450 nm by the cross prism 2018.

<Correction of Linearity Difference of Each LED>

Figure 6:
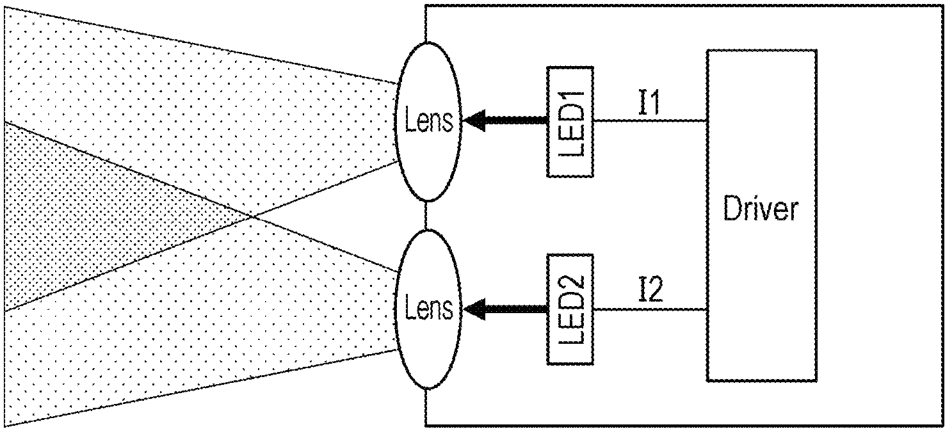
FIG. 6 is a view illustrating a configuration example of a light source using LEDs having different light distribution.

In a case where the light source device 201 includes a plurality of LEDs, not only wavelengths of light emitted from the LEDs 2011 to 2015 but also light distribution (light intensity distribution in each direction) may be different (see FIG. 6: configuration example of light source using LEDs having different light distribution), and there is a possibility that color or light distribution of emitted light from the LEDs 2011 to 2015 may change. In addition, depending on the type of the LED, if a forward voltage is lowered in order to lower the drive current value, the drive current value rapidly decreases and the LED does not emit light, so that the drive current value cannot be able to be greatly lowered. In order to cope with such a situation, it is necessary to dynamically correct a difference in linearity of the emitted light amount/current ratios of the LEDs 2011 to 2015 in accordance with drive current control of the LEDs 2011 to 2015.

Figure 7:
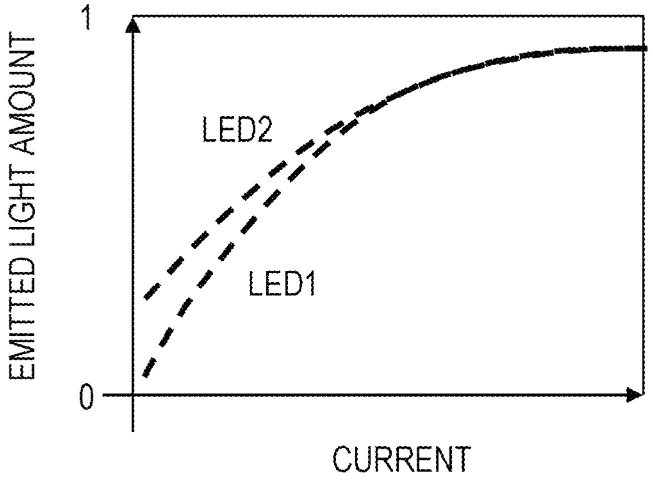
FIG. 7 is a graph of an emitted light amount/current ratio of each LED.

However, processing of dynamically correcting the difference in linearity is complicated, so that it is preferable to determine the drive current value in advance so that there is no difference in linearity. Thus, in the present embodiment, a correction table for correcting the linearity of the emitted light amount/current ratios is prepared in advance, and the drive current values of the LEDs 2011 to 2015 are determined using the correction table. FIG. 7 is a graph of the emitted light amount/current ratio of each LED. FIG. 7 illustrates a relationship between only two LEDs (the LED 1 and the LED 2) as an example, but the same applies to the case of using five LEDs 2011 to 2015 as illustrated in the present embodiment. The relationship between the emitted light amount/current ratio of each LED as illustrated in FIG. 7 can be acquired by measuring each LED in advance. Thus, a correction table having a reciprocal of the relationship between the emitted light amount/current ratio as a correction parameter is provided in advance (stored in a memory) as a correction value, and the light source control unit 2016 multiplies a correction parameter corresponding to a desired emitted light amount (target emitted light amount obtained by exposure adjustment) to calculate a corrected drive current value and drives each LED. This makes it possible to appropriately control the linearity of the emitted light amount/current ratios even in a case where the wavelength and the light distribution of the emitted light of each LED are different.

<Configuration Example of Imaging Surface of Image Sensor>

Figure 8:
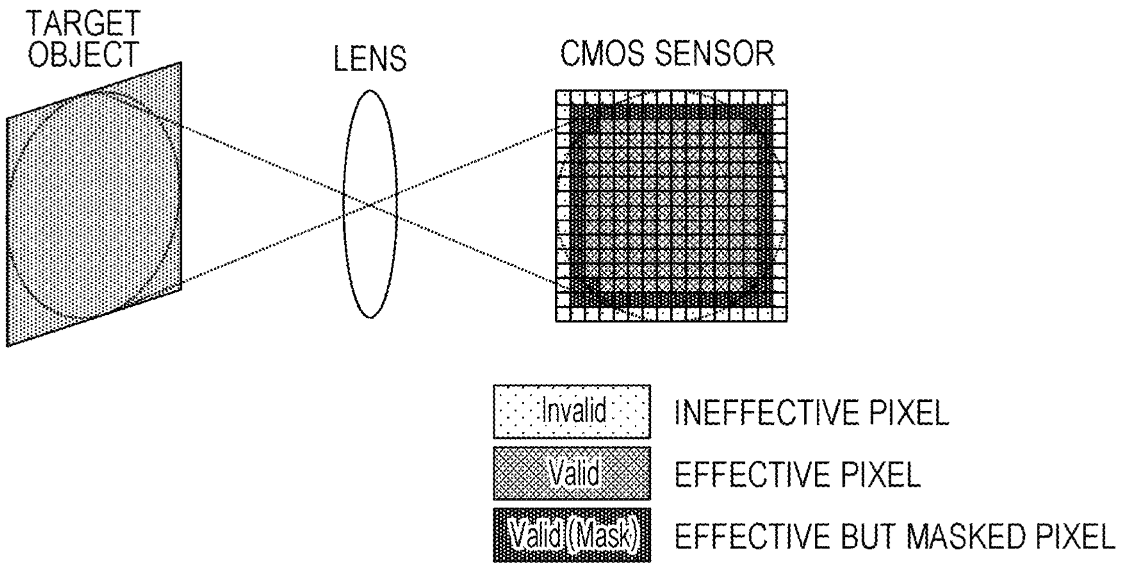
FIG. 8 is a view illustrating an effective pixel region and an ineffective region of a rolling shutter type image sensor using a CMOS sensor as an example.

FIG. 8 is a view illustrating an effective pixel region and an ineffective region of a rolling shutter type image sensor using a CMOS sensor as an example. The CMOS sensor includes an effective pixel region in which imaging can be performed and an ineffective region in which imaging cannot be performed. Furthermore, part (peripheral portion) of the effective pixel region is masked and is a region in which an image signal cannot be substantially acquired. In a case where imaging is performed using such an image sensor (in a case of global exposure), various phenomena (features) appear in the captured image. Note that, in the present embodiment, a period during which an image is not displayed on the screen is the global exposure period, but an idea of the present embodiment is not limited to this case.

<General Dimming Control Processing>

Figure 9:
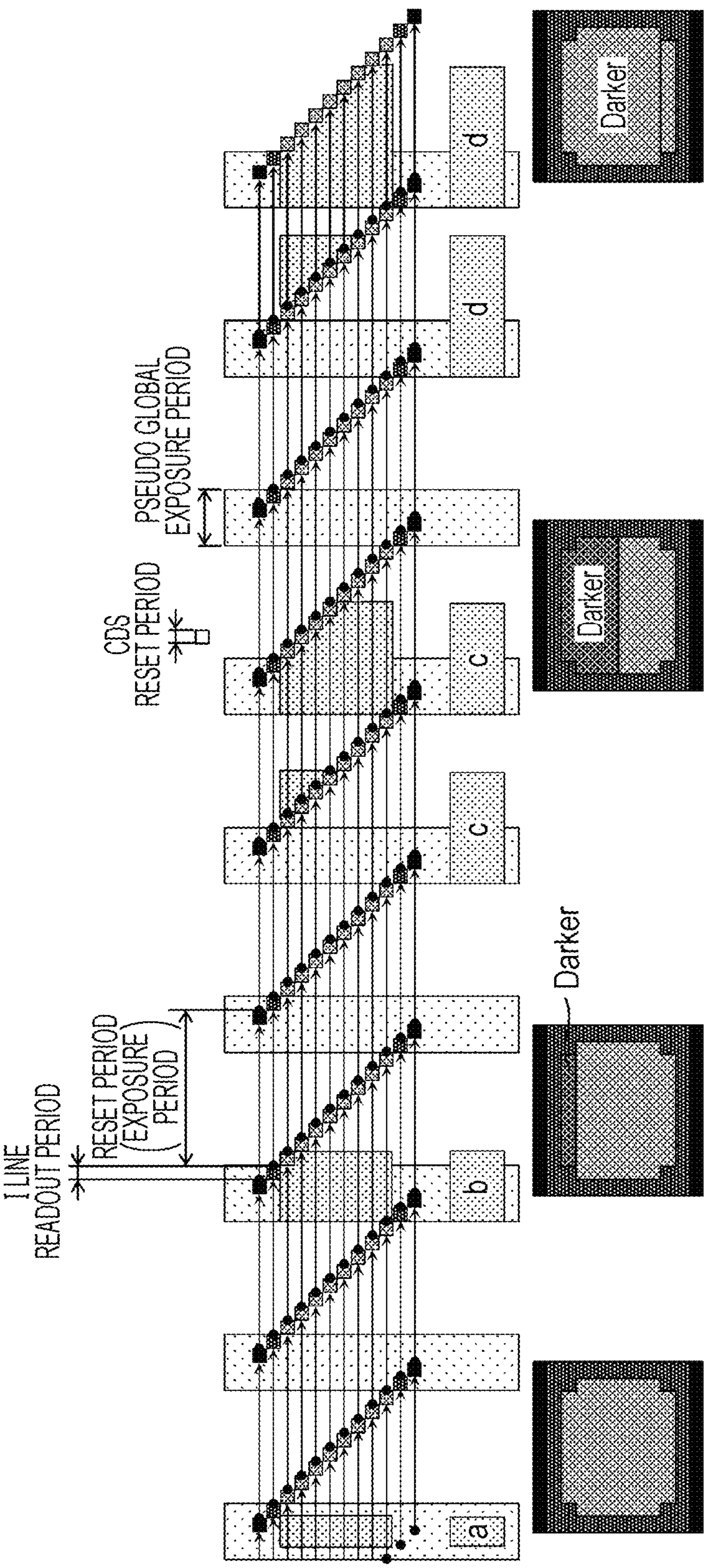
FIG. 9 is a view illustrating a phenomenon (feature) appearing in an image captured using the image sensor having an imaging surface illustrated in FIG. 8 in a case where general dimming control processing is executed.

FIG. 9 is a view illustrating a phenomenon (feature) appearing in an image captured using the image sensor having the imaging surface illustrated in FIG. 8 in a case where general dimming control processing is executed. As illustrated in FIG. 9*a*, if pulse light emission is performed within a readout period of a line not displayed on a screen, pseudo global exposure can be implemented. Furthermore, if pulse light emission is performed as illustrated in FIG. 9*b*, an exposure amount of the uppermost line of the effective pixel region is smaller than that of the other lines by an amount corresponding to a period from reading to resetting, and the uppermost line appears somewhat darker. However, if the period from reading to resetting is sufficiently shorter than the pseudo global exposure period (for example, less than 1%), the darkness is not noticeable. Furthermore, if pulse light emission is performed as illustrated in FIG. 9*c*, about the upper half of the effective pixel region becomes slightly dark, but the darkness of the region becomes further less noticeable as the total exposure amount of each line increases. As described above, as the pulse light emission period increases, the regions having different exposure amounts expand, but the difference in brightness due to the different exposure amounts becomes less noticeable. Furthermore, as illustrated in FIG. 9*d*, if the pulse light emission period is further extended, the ratio smoothly changes from a lower part to an upper part of the screen as the immediately preceding pulse components increase. For this reason, artifacts and distortion (unfavorable phenomena) become less noticeable.

In addition, in a case of the general dimming control processing (FIG. 9), pulse light emission with uniform intensity is performed once for each frame only in part of the pseudo global exposure period (for example, in a case of FIG. 9*a*) or in a continuous period including the entire pseudo global exposure period and part of the rolling shutter period (for example, in a case of FIGS. 9*b* to 9*d*). In a case where a pulse calling period includes the rolling shutter period (in cases of FIGS. 9*b* to 9*d*), an exposure amount of a line read and reset during the pulse light emission decreases by an amount corresponding to the reset period, and lateral stripes may occur at the boundary with other lines. However, if the pulse light emission period is sufficiently larger than the reset period, and the period and the phase are constant and do not change, the lateral stripes are not noticeable.

<Generation of Scanning Line-Like Noise (Vertical Movement of Horizontal Stripes) Due to Expansion/Contraction of Pulse Light Emission Period and Necessity of Pulse Light Emission Period Extension/Shortening Processing>

If an appropriate state of the exposure (exposure) continues and the pulse light emission period is fixed (the pulse light emission profile is fixed), horizontal stripes of light and darkness appearing on the screen do not move (scanning line-like noise does not occur), and thus, the horizontal stripes are not noticeable. However, the exposure (exposure) level of the object actually fluctuates depending on a condition of the object, and thus, it is necessary to extend or shorten the pulse light emission period of illumination light to set an appropriate exposure (exposure) level.

On the other hand, if the pulse light emission period is made to fluctuate, the horizontal stripes move up and down on the screen. This is because change occurs in the ratio between a bright region and a dark region on the screen, so that the lateral stripes appear to be moving. In order to make the movement of the lateral stripes less noticeable, it is necessary to devise extension and shortening processing in the pulse light emission period.

Hereinafter, a case where the pulse light emission period is simply extended and shortened and a technical problem in this case will be described, and subsequently, an idea for improvement to solve the technical problem by simple extension of the pulse light emission period will be described.

<Brightness/Darkness Control by Adjusting Pulse Light Emission Period (Light Amount Reduction and Light Amount Increase Control)>

First, a case where the pulse light emission period is simply extended and shortened in one direction will be described.

(i) Light Amount Reduction Control (FIG. 10): Shortening of the Pulse Light Emission Period (in a Case where the Screen is Too Bright and Desired to be Darkened)

Figure 10:
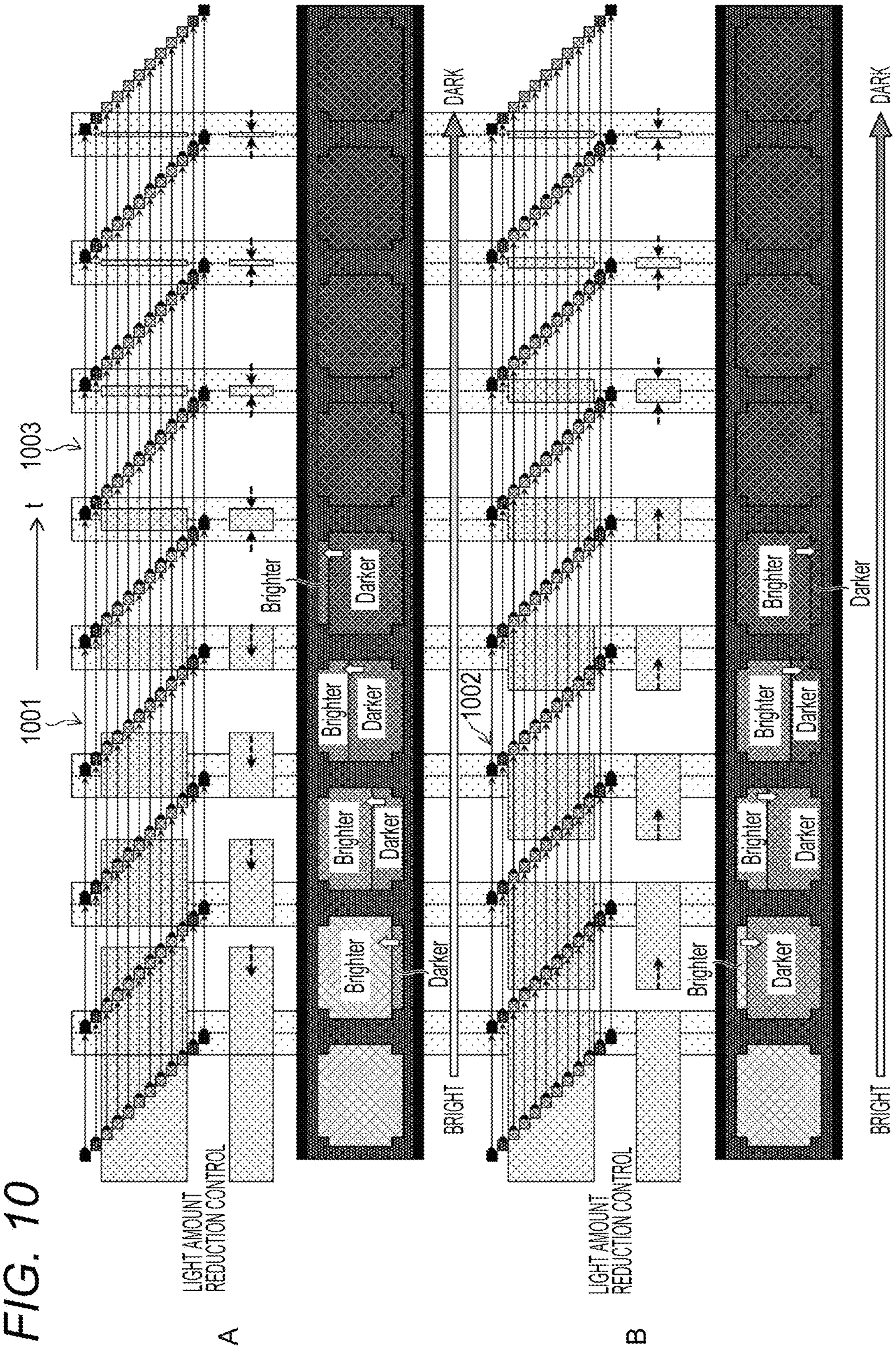
FIG. 10 is a view for explaining light amount reduction control for darkening a screen by shortening a pulse light emission period.

FIG. 10 is a view for explaining light amount reduction control for darkening a screen by shortening the pulse light emission period. The light amount reduction control includes control to shorten the pulse light emission period from the front (from a direction in which time progresses (from the (future) rolling shutter period after the target pseudo global exposure period)) (FIG. 10A) and control to shorten the pulse light emission period from the rear (from a direction in which time has elapsed (from the (past) rolling shutter period before the target pseudo global exposure period)) (FIG. 10B).

As described above, if the pulse light emission period is shortened (the light amount is reduced), an area of the dark region on the screen increases, and lateral stripes (the boundary line between the bright region and the dark region) move up and down, so that presence of the lateral stripes on the screen becomes noticeable. However, depending on the direction (whether to shorten the pulse light emission period from the front or from the rear) in which the pulse light emission period is shortened, there is a difference in its noticeability.

For example, if the fourth frame 1001 in FIG. 10A and the fourth frame 1002 in FIG. 10B are viewed, both the total light emission amounts (light emission intensity×total light emission period) are the same, and thus, the brightness of the screen is the same. However, in these cases, depending on from which direction the pulse light emission period is shortened, there is a difference in a darkening mode (mode at the time of dark change) of the screen. In a case of FIG. 10A, that is, in a case where the pulse light emission period is shortened from the front (direction in which time progresses), the entire screen changes darkly while the dark region increases from the bottom to the top of the screen. On the other hand, in a case of FIG. 10B, that is, in a case where the pulse light emission period is shortened from the rear (direction in which time has elapsed), the entire screen changes darkly while the bright region increases from the top to the bottom. For this reason, a darkening mode in FIG. 10A is natural for the operator, but the darkening mode in FIG. 10B is unnatural. Note that, as in the sixth frame 1003, if the shortened pulse light emission period enters the pseudo global exposure period, the above-described unnatural darkening phenomenon does not occur. Thus, either the pulse light emission period shortening processing of FIG. 10A or 10B may be applied.

Consequently, in a case where at least part of the rolling shutter period is included in the pulse light emission period (in a case where the light emission profile includes at least part of the rolling shutter period), a manner of changing the entire screen to be dark is different depending on the direction in which the pulse light emission period is shortened as described above. It can be therefore seen that it is necessary to shorten the pulse light emission period from the front (it is necessary to adopt the shortening processing of FIG. 10A).

(ii) Light Amount Increase Control (FIG. 11): Extension of the Pulse Light Emission Period (in a Case where the Screen is Too Dark and Desired to be Brightened)

Figure 11:
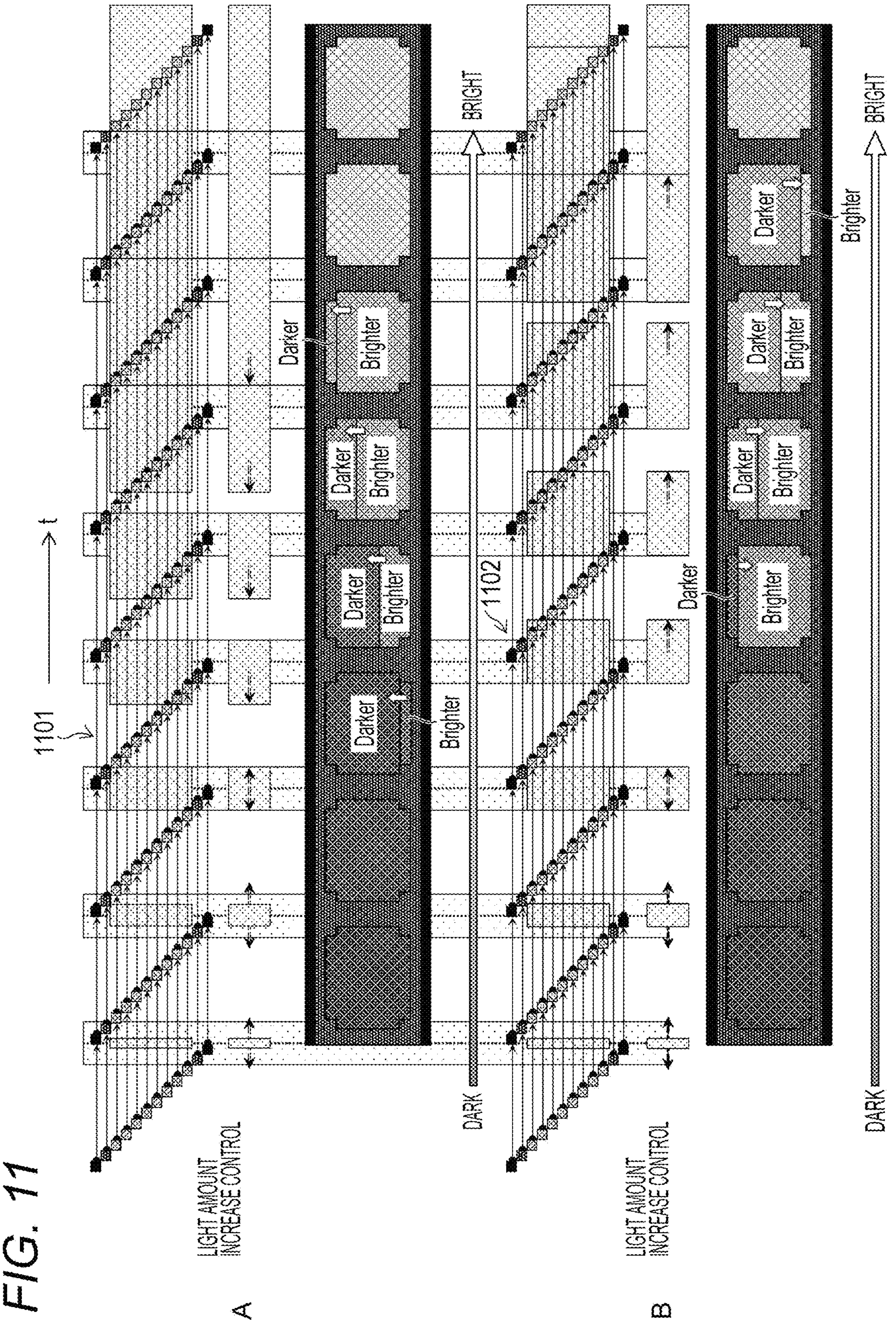
FIG. 11 is a view for explaining light amount increase control for brightening the screen by extending the pulse light emission period.

FIG. 11 is a view for explaining light amount increase control for brightening the screen by extending the pulse light emission period. The light amount increase control includes control to extend the pulse light emission period backward (in a direction in which time has elapsed (to the (past) rolling shutter period before the target pseudo global exposure period)) (FIG. 10A) and control to extend the pulse light emission period forward (in a direction in which time progresses (to the (future) rolling shutter period after the target pseudo global exposure period)) (FIG. 10B).

For example, if the third frame 1101 in FIG. 11A and the fourth frame 1102 in FIG. 11B are viewed, both the total light emission amounts (light emission intensity×total light emission period) are the same, and thus, the brightness of the screen is the same. However, in these cases, depending on from which direction the pulse light emission period is extended, a brightening mode of the screen (a mode at the time of changing brightly) is different. In a case of FIG. 11A, that is, in a case where the pulse light emission period is extended backward (direction in which time has elapsed), the entire screen changes brightly while the bright region increases from the bottom to the top of the screen. On the other hand, in a case of FIG. 11B, that is, in a case where the pulse light emission period is extended forward (in a direction in which time progresses), the entire screen changes brightly while the dark region increases from the top to the bottom. For this reason, the brightening mode in FIG. 11A is natural for the user (operator), but the brightening mode in FIG. 11B is unnatural.

It can be therefore seen that it is necessary to extend the pulse light emission period backward (it is necessary to adopt the extension processing of FIG. 11A) in a case of extending the pulse light emission period.

(iii) Processing of Shortening Pulse Light Emission Interval and then Extending and Processing of Extending Pulse Light Emission Period and then Shortening As described in (i) and (ii) above, it can be seen that it is necessary to shorten the pulse light emission period from the front in a case of shortening the pulse light emission period, and it is necessary to extend the pulse light emission period backward in a case of extending the pulse light emission period.

However, these two kinds of processing are not compatible. For example, if it is desired to brighten the screen from a state of the fourth frame 1001 in FIG. 10A, it is desired to extend the pulse light emission period backward as illustrated in FIG. 11A, but in this case, the rolling shutter period is extended backward in a state where the pulse light emission period exists forward (there is no problem in this extension processing itself). Then, if the condition of the object changes again after the backward extension processing is completed and an appropriate exposure level is reached and it is desired to darken the screen, the pulse light emission period is shortened from the front rolling shutter period according to the processing of FIG. 10A. In this case, the processing is performed from the front, the scanning line-like noise (vertical movement of the horizontal stripes) can be made less noticeable. However, in a case where the front rolling shutter period is not sufficient, there is a possibility that the pseudo global exposure period is reached while the pulse light emission period shortening processing is repeated (until the appropriate exposure (exposure) level is reached). In this event, if it is necessary to further darken, the rolling shutter period in the rear is shortened, but in this case, the scanning line-like noise becomes noticeable and is not appropriate.

Thus, further improvement is required for the processing of extending and shortening the pulse light emission period.

<Improved Pulse Light Emission Period Adjustment (Extension and Shortening) Processing>

Figure 12:
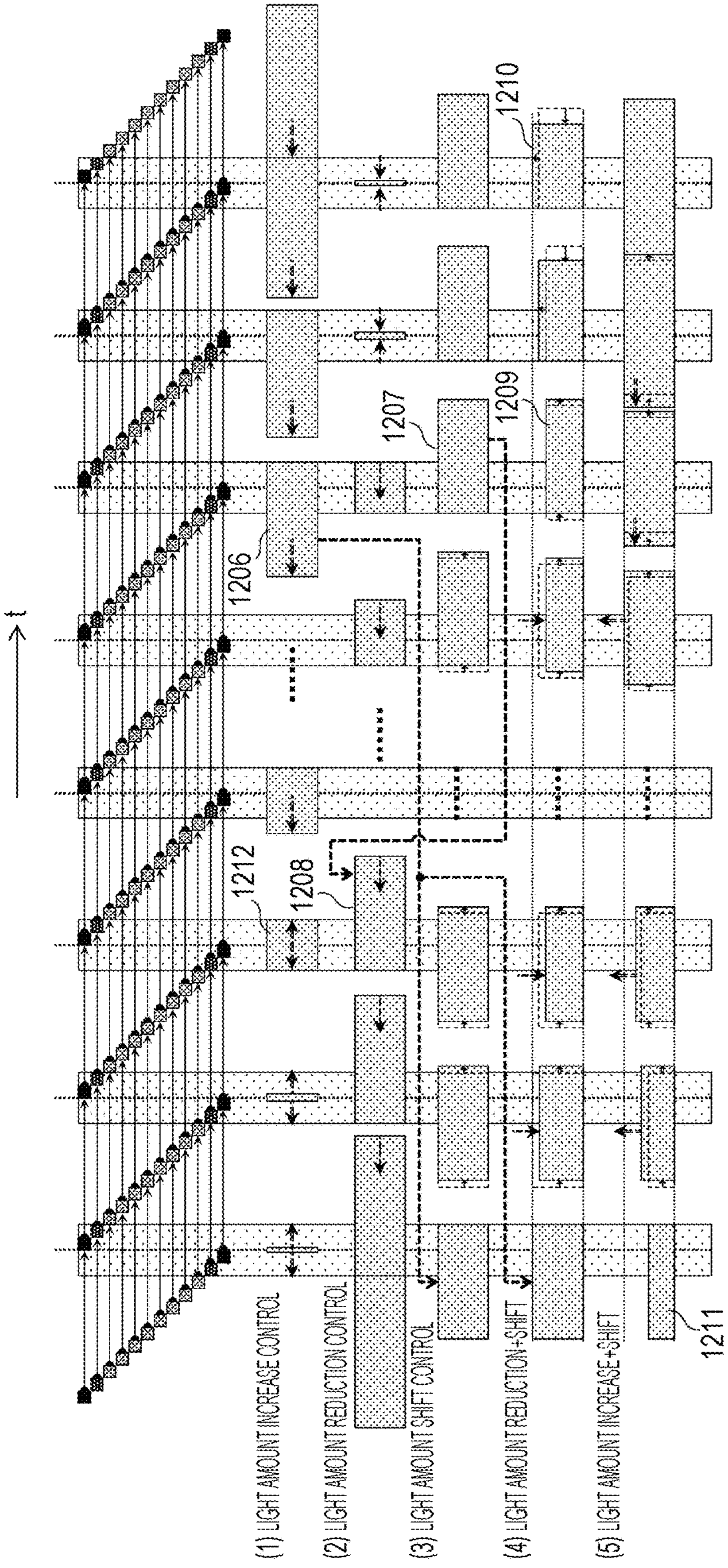
FIG. 12 is a view illustrating outline of improved pulse light emission period adjustment processing.

FIG. 12 is a view illustrating outline of the improved pulse light emission period adjustment processing. Also in the improved pulse light emission period adjustment processing, in order to make the scanning line-like noise (vertical movement of horizontal stripes) on the screen less noticeable, the pulse light emission period is extended backward (similar to FIG. 10A) to brighten the screen (increase the light amount), and conversely, the pulse light emission period is shortened from the front (similar to FIG. 11A) to darken the screen (reduce the light amount). This adjustment operation is illustrated in FIG. 12(1) Light amount increase control and FIG. 12(2) Light amount reduction control.

For example, if it is desired to reduce the light amount from a state of the light emission profile 1206 to darken the screen, the rolling shutter period is not included in front of the light emission profile 1206, and thus, the light amount reduction control of FIG. 12(2) (=FIG. 10A) cannot be executed. Thus, before the light amount reduction processing (FIG. 12(2)) is executed, the light amount shift control processing (FIG. 12(3)) is executed to shift the light emission amount in the rear rolling shutter period to the front rolling shutter period. In this case, the shift operation is controlled such that the total amount of light (the area of the light emission profile) is the same between before and after the shift. The light amount shift control processing is completed by allocating the entire light emission amount in the rear rolling shutter period to the front rolling shutter period. Thus, the light emission profile 1206 is adjusted by the light amount shift control processing like the light emission profile 1207 in which the light emission intensity and the light emission period length are the same. Then, the light amount reduction control processing is executed from the light emission profile 1208 (same as the light emission profile 1207) adjusted to this state, and the pulse light emission period of the rolling shutter period is shortened from the front.

The light amount shift control processing is executed over a long period (the light emission profile is changed from 1206 to 1207 over a long period), and thus, the operator may want to immediately darken the screen (rapidly darken the screen) without waiting for completion of the light amount shift control processing. In order to cope with such a case (scene), the light amount shift control processing and the light amount reduction control processing can be executed simultaneously (FIG. 12(4): light amount reduction+shift). However, in FIG. 12(4), the light amount is reduced not by shortening the pulse light emission period but by lowering the light emission intensity level. In this case, processing of reducing the light emission intensity over the entire pulse light emission period is performed while shifting the light amount in the rear rolling shutter period to the front rolling shutter period. What is important here is that not only the intensity is simply lowered, but also the light amount shift control processing is continuously executed in parallel. This is because the pulse light emission period cannot be shortened in the time direction (the light amount reduction processing cannot be executed) unless the light amount shift control processing is executed. Then, if the shifting operation of the total amount of light in the rear rolling shutter period to the front rolling shutter period is completed (after conversion into the light emission profile 1209), the light emission profile 1210 is formed by allocating (increasing to the maximum value of the light emission intensity) the amount of light in the rolling shutter period for increasing the light emission intensity while keeping the total amount of light (area of light emission profile=light emission intensity×pulse light emission period length) constant. After the state becomes a state of the light emission profile 1210, the front rolling shutter period may be shortened (FIG. 12(2)) in order to darken the screen, and the rolling shutter period may be extended backward (FIG. 12(1)) in order to brighten the screen. Note that the light emission profile may include a pulse light emission period in the front rolling shutter period. In this case, the light amount reduction control processing (the process of FIG. 12(2)) may be immediately executed.

On the other hand, there is also a case (scene) where the imaging condition of the object changes during execution of the light amount reduction+shift processing (FIG. 12(4)), and it is desired to immediately brighten the screen (it is desired to quickly blink the screen). In this case, it is possible to brighten the screen (increase the exposure level) by simultaneously executing the light amount shift control processing and the light amount increase control processing from a state where the light emission intensity level is not at the maximum value (light emission profile 1211) ((FIG. 12(5): light amount increase+shift). However, in FIG. 12(5), the light amount is increased not by extending the pulse light emission period but by increasing the light emission intensity level. For example, in a case where it is desired to increase the light amount from the light emission profile 1211 to brighten the screen, as illustrated in FIG. 12(5), the light intensity level is increased from the light emission profile 1211, and at the same time, the light amount in the rear rolling shutter period is shifted to the front rolling shutter period. Then, this operation is repeated until the light emission intensity level reaches the maximum value and the entire light amount in the rear rolling shutter period is shifted to the front rolling shutter period. If the light emission intensity level is the maximum value and the exposure (exposure) level of the light emission profile (not illustrated) at the time of completion of the light amount shift is appropriate, the processing is completed. On the other hand, in a case where it is desired to further brighten the screen from this state, the pulse light emission period is extended backward (the processing of FIG. 12(1) is executed). Furthermore, in a case where it is desired to darken the screen again from this state, the pulse light emission period is shortened from the front (the processing of FIG. 12(2) is executed). Note that the light emission profile may not include the pulse light emission period in the rear rolling shutter period. In this case, the light amount increase control processing (the processing of FIG. 12(1)) may be executed after the processing of increasing the light intensity level to the maximum value is executed without executing the light amount shift processing.

<Improved Pulse Light Emission Period Adjustment (Extension and Shortening) Processing: Use Case (Series of Flows)>

(i) In a case where a distance between the object and the distal end portion 12 of the endoscope device 100 is increased from the state where the pulse light emission period is shortened (for example, the emission profile 1212

(see FIG. 12(1))), and it becomes a situation where it is desired to increase the light because the screen becomes dark, the light amount increase control processing (FIG. 12(1)) is executed, and the pulse light emission period is extended backward of the pseudo global exposure period (in a direction of the past rolling shutter period). In a case where it is desired to reduce the light because the distance between the object and the distal end portion 12 of the endoscope device 100 approaches while the pulse light emission period is being extended (or in a state where the light amount shift control processing is not completed although the extension is stopped as a result of reaching appropriate brightness) and the screen becomes excessively bright, the light amount shift control processing is not completed and there is no pulse light emission period in front of the pseudo global exposure period (in a direction in which time progresses), and thus, the light amount reduction control processing (FIG. 12(2)) cannot be executed. Thus, the light amount reduction control processing for reducing the light emission intensity level and the light amount shift control processing are simultaneously executed (FIG. 12(4)) to make the screen brightness appropriate. Furthermore, in a case where the object and the distal end portion 12 of the endoscope device 100 move away from each other again before the pulse components obtained by shifting the light amount during the front rolling shutter period are reduced to the light emission intensity to reach the state in which the decrease in intensity is eliminated (for example, the emission profile 1210), and it is desired to increase the light because the screen becomes dark, a state in which the decrease in intensity is not eliminated continues if the light amount increase control processing (FIG. 12(1)) is immediately executed. Thus, in order to return the intensity to the maximum value once before the light amount increase control processing is executed, the light amount increase processing of increasing the light emission intensity level and the light amount shift control processing are simultaneously executed (FIG. 12(5)).

(ii) In a case where the distance between the object and the distal end portion 12 of the endoscope device 100 becomes short and the screen becomes excessively bright, and thus, it is desired to reduce the light, the light emission intensity level may be lowered without executing the light amount shift control processing to darken the screen. In this event, for example, the light emission profile 1206 can be changed to the light emission profile 1211. In this state (light emission profile 1211), in a case where it is desired to brighten the screen again, the light amount increase control processing (FIG. 12(1)) is not immediately executed, but the light amount increase processing of increasing the light emission intensity level and the light amount shift control processing are simultaneously executed (FIG. 12(5)). In a case where the light emission intensity level has reached the maximum value but has not reached the desired brightness, it is possible to execute light amount increase control processing (FIG. 12(1)) of extending the pulse light emission period backward.

<Shift Amount in One Light Amount Shift Control Processing>

In a case where the pulse light emission period is set over the entire (rear) rolling shutter period one frame before the pseudo global exposure period of the target frame, the above-described light amount shift control processing (see FIG. 12(3)) is executed to shift all the pulse light emission periods to the (front) rolling shutter period of the current frame, for example, over about 1 second. In other words, a maximum period taken until the shift operation is completed is one second. For example, in a case where the number of frames captured per second is 60 frames, a period required for one shift operation is 1/60 seconds. In a case where 30 frames are captured in 1 second, a period required for one shift operation is 1/30 seconds.

By slowly execute the light amount shift control processing over a long period in this manner, the scanning line-like noise can be made less noticeable.

<Offset Light Emission Processing>

Figure 13:
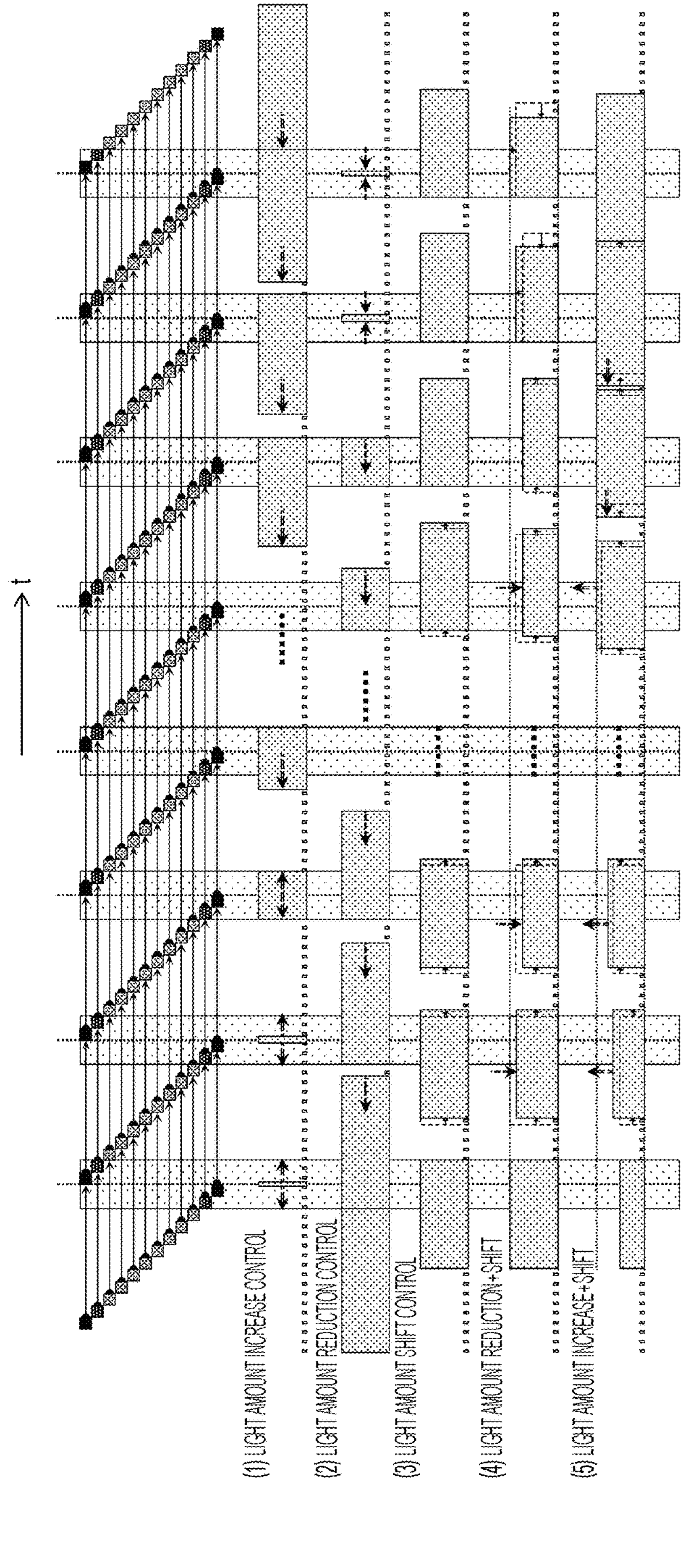
FIG. 13 is a view for explaining offset light emission processing in a non-light emission period (or a weak light emission period in which light emission intensity is so weak that light emission cannot be visually recognized).
Figure 14:
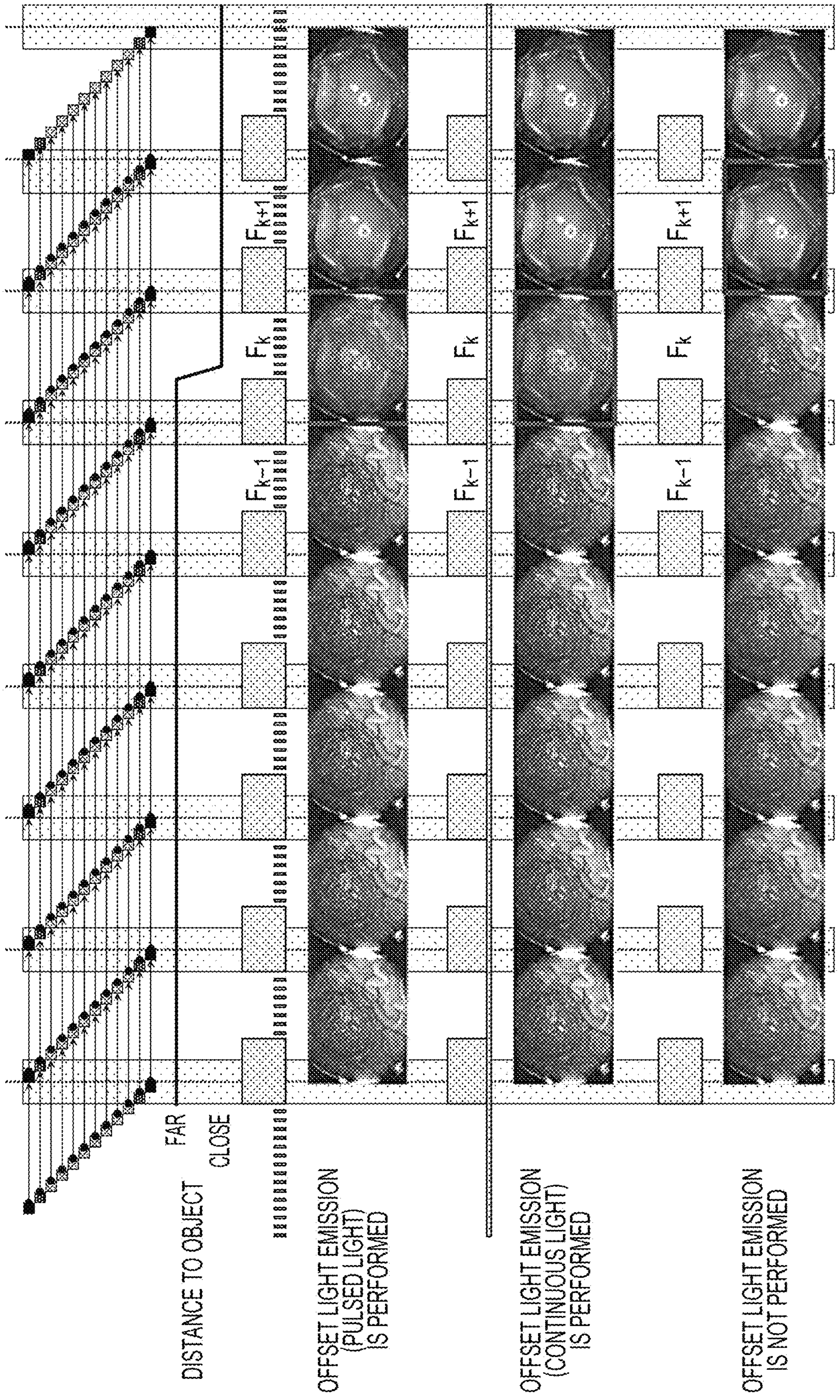
FIG. 14 is a view illustrating a difference between captured images that appears depending on whether or not offset light emission is performed when the image sensor suddenly approaches an object.

FIGS. 13 and 14 are views for explaining offset light emission processing in a non-light emission period (alternatively, a weak light emission period in which the light emission intensity is so weak that light emission cannot be visually recognized). FIG. 13 illustrates offset light emission by a weak pulse. FIG. 14 is a view illustrating a difference between captured images that appear depending on whether or not offset light emission is performed when the image sensor suddenly approaches the object. Here, "weak" means that the light emission intensity is sufficiently lower than the light emission intensity in the strong light emission period, but the light emission intensity is such that the light emission can be visually recognized. In the present embodiment, the weak pulse is exemplified as the offset light emission, but the weak continuous light emission may be used, or a light emission pattern other than the weak pulse light emission and the weak continuous light emission may be used. For example, a light emission pattern may be configured by combining the pulse light emission and the continuous light emission, or a light emission pattern with an irregular pulse width may be configured.

The offset light emission processing is processing that is to be executed separately from the dimming control processing in related art (such as FIG. 9) and the pulse light emission period adjustment (dimming control) processing (see FIG. 12) according to the present embodiment (in the background of the dimming control processing) and is processing of performing weak offset light emission during the non-light emission period. The weak offset light emission can be regarded as 0 (zero) in a case where the intensity of light emission by the dimming control processing (applicable to any dimming control processing) is a predetermined value or more. On the other hand, if the intensity of light emission by the dimming control processing is less than the predetermined value (or if the light emission intensity is zero), the object is irradiated only with offset light emission. As a result, although an event that has originally occurred in the non-light emission period cannot be acquired as an image, the event occurring in the non-light emission period can be captured by offset light emission.

Referring to FIG. 14, in a case where there is no weak offset light emission, the same image as a frame Fk−1 is acquired as a captured image of a frame Fk. On the other hand, in a case where the weak offset light emission is performed, the captured image of the frame Fk is an image clearly different from the frame Fk−1 in either case of the pulsed light or the continuous light, and it can be seen that an event when the image sensor suddenly approaches the object in the frame Fk is captured. In addition, it can be seen that a captured image of a frame Fk+1 does not differ depending on whether or not weak offset light emission is performed.

<Pulse Light Emission Period Adjustment (Dimming Control) Processing: Flowchart>

FIG. 15 is a flowchart for explaining dimming control processing according to the present embodiment. Although the processing of each of the following steps has been mainly described with the system controller 202 as an operation subject, the present disclosure is not limited thereto, and a control unit (processor) that performs operation control and arithmetic processing may be separately provided and may be caused to perform execution. Furthermore, functions of the system controller 202 may be provided to the light source control unit 2016 of the light source device 201. Thus, the dimming (reduction) control processing can be made part of the entire operation of the endoscope system 1 or can be made part of the operation of the light source device 201. In this case, the light source control unit 2016 is a main operation subject of the processing of each step.

(i) Step 1501

The light source control unit 2016 receives a mode selection signal corresponding to the observation mode selected by the operator from the system controller and corrects the linearity of the emitted light amount/current ratio of each light source for each light source (any combination of the green LED 2011 to the UV LED 2015) to emit light using the correction table.

(ii) Step 1502

The light source control unit 2016 drives each light source with the drive current after the linearity of the emitted light amount/current ratio is corrected to cause each light source to emit light to generate illumination light and irradiates the object with the illumination light. Note that the light emission profile (the period of strong light emission and the level and period of weak light emission) in this event can be set at a predetermined value (default value), or the light emission profile used in the last operation at the time of using the endoscope at the previous time can be used.

(iii) Step 1503

The image sensor (for example, a CMOS sensor) of the imaging unit 103 detects reflected light from the object generated by irradiating the object (observation site) with the illumination light generated in step 1702 and transmits a captured image signal to the processor 200 via the scope connector circuit 401. The photometry unit 203 acquires luminance information of a current captured image signal from a gain circuit included in the color conversion circuit 206, compares (for example, obtains a difference value) the acquired luminance information with a predetermined appropriate luminance value and passes a comparison result to the system controller 202. Note that the photometry unit 203 may acquire only the luminance information of the current captured image signal from the gain circuit, and the comparison with the appropriate luminance value may be executed by another processing unit such as the system controller 202.

(iv) Step 1504

The system controller 202 compares the comparison result (alternatively, the system controller 202 may calculate the comparison result (difference value)) received from the photometry unit 203 with a predetermined threshold value (threshold value for determining whether the exposure level is appropriate) and determines whether the current exposure level is appropriate. For example, if the comparison result (difference value) is equal to or less than the predetermined threshold value, it can be determined that the comparison result is appropriate. In a case where it is determined that the current exposure level is not appropriate (No in step 1504), the processing proceeds to step 1507. On the other hand, in a case where it is determined that the current exposure level is appropriate (Yes in step 1504), the processing proceeds to step 1505.

(v) Step 1505

The light source control unit 2016 receives information of the light emission profile to be applied from the system controller 202 and generates illumination light by causing any one of the LEDs 2011 to 2015 to emit light on the basis of the received light emission profile and mode selection signal to irradiate the object with the illumination light. Furthermore, the image sensor (CMOS sensor) of the imaging unit 103 detects reflected light from the object irradiated with the illumination light, generates a captured image signal and transmits the captured image signal to the processor. Furthermore, the processor 200 executes predetermined image processing on the captured image signal to generate display image data and displays the display image data on the screen of the monitor (display device) 300.

(vi) Step 1506

The system controller 202 determines whether an instruction to end observation such as end of imaging or turning off of illumination light is input from the operator. In a case where an instruction to end the observation is input (YES in step 1506), the dimming control processing ends. In a case where the instruction to end the observation is not input (the instruction is not detected) (in a case of NO in step 1506), the processing proceeds to step 1503, and determination/monitoring as to whether or not the current exposure level is appropriate, dimming control processing, and the like, are continuously performed. The imaging unit 103 is installed at the distal end portion 12 of the endoscope device 100 and moves in the body cavity of the object. Thus, the exposure level may change because the image sensor approaches or moves away from the object (observation site). Thus, the operation of the light source device 201 is controlled so as to constantly monitor the luminance level of the captured image and maintain an appropriate exposure level.

(vii) Step 1507

The system controller 202 determines whether the operator gives an instruction to rapidly change brightness. In a case where the brightness/darkness of the screen is changed by adjusting the light amount, normally, the light amount increase control processing (FIG. 12(1)) or the light amount reduction control processing (FIG. 12(2)) is executed after the light amount shift control processing ends (FIG. 12(3)). However, depending on the observation situation of the object, it may be necessary to change the brightness before the entire light amount in the rear rolling shutter period is shifted to the front rolling shutter period. Thus, in a case where rapid brightness change processing is required, the brightness change is implemented by the light emission intensity in addition to the light amount shift control processing (FIGS. 12(4) and (5))

If rapid brightness change is performed (YES in step 1507), the processing shifts to step 1513. On the other hand, in a case where the rapid brightness change is not performed (NO in step 1507), the processing proceeds to step 1508.

(viii) Step 1508

The system controller 202 determines whether the operator gives an instruction to brighten the screen or gives an instruction to darken the screen. In a case where the operator gives an instruction to brighten the screen, the processing proceeds to step 1509. On the other hand, in a case where the operator gives an instruction to darken the screen, the processing proceeds to step 1511. Note that, in addition to the instruction of the operator, the photometry unit 203 may measure the luminance value level in the captured image and automatically determine whether to increase or decrease the exposure level.

(ix) Step 1509

In a case where the operator gives an instruction to brighten the screen, the system controller 202 executes the light amount increase control processing to extend the pulse light emission period of the current light emission profile (increase the light amount). In other words, as illustrated in FIG. 12(1), the system controller 202 extends the pulse light emission period of the rear rolling shutter period and increases the total light amount of the light emission profile until the brightness reaches desired brightness.

(x) Step 1510

With respect to the light emission profile changed in step 1509, the system controller 202 shifts the light amount of the pulse light emission period in the rolling shutter period (the rolling shutter period of the previous frame) after the pseudo global exposure period (in a direction in which time has elapsed) to the front rolling shutter period (the rolling shutter period of the current frame) (in a direction in which time progresses). In this event, the shift operation is controlled such that the total amount of light (light emission intensity× pulse light emission period=area of light emission profile) in the light emission profile becomes the same between before and after the shift (see FIG. 12(3)).

The light amount shift control processing is executed until all the light emission components in the rear rolling shutter period are shifted (allocated) to the front rolling shutter period. The amount of light shifted in one operation can be determined to an amount by which the amount of light determined by the total rolling shutter period×the maximum value of the emission intensity in one frame can be shifted in a predetermined period. For example, in a case where the predetermined period is 1 second and 60 frames are captured in 1 second, the amount of light shifted at one time can be set to (the amount of light determined by the total rolling shutter period×the maximum value of the light emission intensity in one frame)/60.

In a case of brightening the screen, the light amount is first increased (step 1509) because the scanning line-like noise is not noticeable even if the pulse light emission period is extended forward, and the light amount is then shifted (step 1510) because it is possible to appropriately execute the light amount increase/reduction processing (without making the scanning line-like noise noticeable) later.

After step 1510, the processing proceeds to step 1503.

(xi) Step 1511

In a case where the operator gives an instruction to darken the screen, the system controller 202 first shifts the light amount of the pulse light emission period in the rolling shutter period (rolling shutter period of the previous frame) after the pseudo global exposure period (in a direction in which time has elapsed) to the front rolling shutter period (rolling shutter period of the current frame) (in a direction in which time progresses) with respect to the (current) light emission profile before the change (see FIG. 12(3)).

(xii) Step 1512

The system controller 202 executes the light amount reduction control processing on the light emission profile whose light amount has been shifted in step 1511, thereby shortening the pulse light emission period of the light emission profile (reducing the light amount). In other words, as illustrated in FIG. 12(2), the system controller 202 shortens the pulse light emission period in the front rolling shutter period and decreases the total light amount of the light emission profile until desired darkness is obtained.

After step 1512, the processing proceeds to step 1503.

(xiii) Step 1513

In a case of darkening the screen, the system controller 202 shifts light amount components (light emission components) of the pulse light emission period in the rear rolling shutter period to the pulse light emission period in the front rolling shutter period while lowering the pulse light emission intensity (see FIG. 12(4)). As a result, the rear pulse light emission period is shortened, the front pulse light emission period is extended, and the pulse light emission intensity is reduced, so that two kinds of operation of the screen darkening and the light amount shift can be simultaneously executed, and the screen can be rapidly darkened. In a case where the front rolling shutter period becomes equal to or greater the predetermined period and an appropriate exposure level is reached by the light amount shift operation, the system controller 202 replaces the light amount (pulse light emission components) in the front pulse light emission period increased by the shift until the pulse light emission intensity becomes the maximum value. In other words, the pulse light emission period is shortened while the identity of the total light amount (the area of the light emission profile) is maintained, and the pulse light emission intensity is increased. As a result, the light emission profile obtained by simultaneously executing the pulse light emission intensity reduction processing and the light amount shift control processing (FIG. 12(4)) becomes the same as the light emission profile obtained by executing the light amount shift control processing (FIG. 12(3)) and then executing the light amount reduction control processing (FIG. 12(2)).

On the other hand, in a case of brightening the screen, the system controller 202 shifts the light amount components (light emission components) of the pulse light emission period in the rear rolling shutter period to the pulse light emission period in the front rolling shutter period while increasing the pulse light emission intensity (see FIG. 12(5)). If the pulse light emission intensity reaches a maximum value before reaching the desired brightness, the system controller 202 extends the pulse light emission period in the direction of the rear rolling shutter period (until reaching the desired brightness). As a result, the light emission profile obtained by simultaneously executing the pulse light emission intensity increase processing and the light amount shift control processing (FIG. 12(5)) becomes the same as the light emission profile obtained by executing the light amount increase control processing (FIG. 12(1)) and then executing the light amount shift control processing (FIG. 12(3)).

Effects of Present Embodiment

According to the present embodiment, it is possible to capture an image of an object while securing a sufficient light amount while avoiding rolling shutter distortion and artifacts. In addition, even if the change in the pulse light emission period extends over the rolling shutter period, the vertical movement of the lateral stripes can be made less noticeable. Furthermore, in a case where a plurality of LEDs are simultaneously used as the light source, if the light emission intensity changes, the ratio of the light amount of each LED changes unless the current control is performed by correcting the difference in the linearity of the emitted light amount/current ratio of each LED, and the light distribution changes and the color changes. However, according to the present embodiment, the light emission intensity can be returned in a short period, and such a problem can be solved.

<Specified Matters of Present Disclosure>

(1) Specified Matter 1

A light source device that generates illumination light with which an object is to be irradiated, the light source device including:

a plurality of semiconductor light emitting elements configured to emit light having different wavelength bands, and a control unit configured to control a light emission profile of the plurality of semiconductor light emitting elements and drive the plurality of semiconductor light emitting elements, in which the control unit extends the light emission profile in a first direction that is a direction opposite to a direction in which time progresses in a case of increasing an exposure level and shortens the light emission profile from a second direction that is the direction in which time progresses in a case of decreasing the exposure level.

(2) Specified Matter 2

The light source device in the specified matter 1, in which the light emission profile defines (i-1) a period in which the illumination light is emitted in at least part of a pseudo global exposure period of an image sensor that captures an image of the object, or (ii-2) a pulse light emission period indicating a period in which the illumination light is emitted in at least part of the pseudo global exposure period and a rolling shutter period of the image sensor, and (ii) pulse light emission intensity indicating intensity of the illumination light in the pulse light emission period.

(3) Specified Matter 3

The light source device in the specified matter 2, in which in a case of increasing the exposure level, after extending the light emission profile in the first direction, the control unit shifts a light emission component in a rolling shutter period in the first direction relative to the pseudo global exposure period to a light emission component in a rolling shutter period in the second direction relative to the pseudo global exposure period to change the light emission profile.

(4) Specified Matter 4

The light source device in the specified matter 2, in which in a case of decreasing the exposure level, the control unit shifts a light emission component in a rolling shutter period in the first direction relative to the pseudo global exposure period to a light emission component in a rolling shutter period in the second direction relative to the pseudo global exposure period to change the light emission profile, and then, shortens a pulse light emission period of the changed light emission profile from the second direction.

(5) Specified Matter 5

The light source device in the specified matter 2, in which the control unit shifts a light emission component of a rolling shutter period in the first direction relative to the pseudo global exposure period to a rolling shutter period in the second direction relative to the pseudo global exposure period while increasing the pulse light emission intensity in a case where the control unit is instructed to rapidly increase the exposure level in a state where the pulse light emission intensity has decreased from a predetermined maximum value.

(6) Specified Matter 6

The light source device in the specified matter 2, in which the control unit shifts a light emission component of a rolling shutter period in the first direction relative to the pseudo global exposure period to a rolling shutter period in the second direction relative to the pseudo global exposure period while decreasing the pulse light emission intensity in a case where the control unit is instructed to rapidly decrease the exposure level.

(7) Specified Matter 7

The light source device in the specified matter 6, the control unit replaces the light emission component in the rolling shutter period in the second direction with increase in the pulse light emission intensity so that the pulse light emission intensity becomes a predetermined maximum value after the rolling shutter period in the second direction becomes equal to or greater than a predetermined period and an appropriate exposure level is reached by shift operation of the light emission component from the rolling shutter period in the first direction to the rolling shutter period in the second direction.

(8) Specified Matter 8

The light source device in any one of the specified matters 1 to 7, in which the control unit further executes processing of correcting linearity of emitted light amount/current ratios of the plurality of semiconductor light emitting elements.

(9) Specified Matter 9

The light source device in any one of the specified matters 1 to 8, in which the control unit executes offset light emission with pulsed light or continuous light in addition to light emission by the light emission profile.

(10) Specified Matter 10

An endoscope system that inserts an endoscope into an observation target and acquires an image of an object, the endoscope system including:

a plurality of semiconductor light emitting elements configured to emit light having different wavelength bands, an image sensor configured to irradiate the object with illumination light and detect reflected light from the object to generate an image signal, a processor configured to process the image signal to generate the image of the object and display the image on a monitor, a main control unit configured to generate a control signal for controlling a light emission profile of the plurality of semiconductor light emitting elements on the basis of the image signal, and a light source control unit configured to receive the control signal from the main control unit and drive the plurality of semiconductor light emitting elements with a drive signal according to the light emission profile, in which the light emission profile defines (i-1) a period in which the illumination light is emitted in at least part of a pseudo global exposure period of the image sensor that captures the image of the object, or (ii-2) a pulse light emission period indicating a period in which the illumination light is emitted in at least part of the pseudo global exposure period and a rolling shutter period of the image sensor, and (ii) pulse light emission intensity indicating intensity of the illumination light in the pulse light emission period, and the main control unit extends the light emission profile in a first direction that is a direction opposite to a direction in which time progresses in a case of increasing an exposure level and shortens the light emission profile from a second direction that is the direction in which time progresses in a case of decreasing the exposure level.

(11) Specified Matter 11

The endoscope system in the specified matter 10, in which in a case of increasing the exposure level, after extending the light emission profile in the first direction, the main control unit shifts a light emission component in a rolling shutter period in the first direction relative to the pseudo global exposure period to a light emission component in a rolling shutter period in the second direction relative to the pseudo global exposure period to change the light emission profile.

(12) Specified Matter 12

The endoscope system in the specified matter 10, in which in a case of decreasing the exposure level, the main control unit shifts a light emission component in a rolling shutter period in the first direction relative to the pseudo global exposure period to a light emission component in a rolling shutter period in the second direction relative to the pseudo global exposure period to change the light emission profile, and then, shortens a pulse light emission period of the changed light emission profile from the second direction.

(13) Specified matter 13

The endoscope system in the specified matter 10, in which the main control unit shifts a light emission component of a rolling shutter period in the first direction relative to the pseudo global exposure period to a rolling shutter period in the second direction relative to the pseudo global exposure period while increasing the pulse light emission intensity in a case where the main control unit is instructed to rapidly increase the exposure level in a state where the pulse light emission intensity has decreased from a predetermined maximum value.

(14) Specified Matter 14

The endoscope system in the specified matter 10, in which the main control unit shifts a light emission component of a rolling shutter period in the first direction relative to the pseudo global exposure period to a rolling shutter period in the second direction relative to the pseudo global exposure period while decreasing the pulse light emission intensity in a case where the main control unit is instructed to rapidly decrease the exposure level.

(15) Specified Matter 15

The endoscope system in the specified matter 14, in which the main control unit replaces the light emission component in the rolling shutter period in the second direction with increase in the pulse light emission intensity so that the pulse light emission intensity becomes a predetermined maximum value after the shift operation of the light emission component from the rolling shutter period in the first direction to the rolling shutter period in the second direction is completed and an appropriate exposure level is reached.

REFERENCE SIGNS LIST

1 Endoscope system
100 Endoscope device
103 Imaging unit
200 Processor
201 Light source device
2011 Green LED
2012 Blue LED
2013 Red LED
2014 Amber LED
2015 UV LED
2016 Light source control unit
2017, 2018 Cross prism
202 System controller
203 Photometry unit
300 Monitor

The invention claimed is:

1. A light source device that generates illumination light with which an object is irradiated, the light source device comprising:

a plurality of semiconductor light emitting elements configured to emit light having different wavelength bands; and a controller configured to control a light emission profile of the plurality of semiconductor light emitting elements and drive the plurality of semiconductor light emitting elements, wherein the light emission profile defines (i-1) a pulse light emission period indicating a period in which the illumination light is emitted in at least a part of a pseudo global exposure period of an imaging element that images the subject or (i-2) a period in which the illumination light is emitted in at least a part of a pseudo global exposure period and a rolling shutter period of the imaging element, and (ii) a pulse light emission intensity indicating an intensity of the illumination light in the pulse light emission period, wherein in a case where an exposure level is increased, the controller extends the light emission profile in a first direction that is a direction opposite to a direction in which time progresses, wherein in a case where the exposure level is lowered, the controller shortens the pulse light emission period of the light emission profile from a second direction which is an advancing direction of time, and wherein in the case where the exposure level is lowered, when the light emission profile does not include light emission of the rolling shutter period in the second direction, while keeping a total light emission amount indicated by the light emission profile the same, the controller changes a light emission component in a rolling shutter period in the first direction with respect to the pseudo global exposure period to a light emission component in a rolling shutter period in the second direction with respect to the pseudo global exposure period, and after the controller changes the light emission profile by shifting to a light emission component in a certain rolling shutter period, the controller shortens a pulse light emission period of the light emission profile after the change from the second direction.

2. The light source device according to claim 1, wherein in a case of increasing the exposure level, after extending the light emission profile in the first direction, the controller shifts a light emission component in a rolling shutter period in the first direction relative to the pseudo global exposure period to a light emission component in a rolling shutter period in the second direction relative to the pseudo global exposure period to change the light emission profile.

3. The light source device
according to claim 1,
wherein the controller shifts a light emission component of a rolling shutter period in the first direction relative to the pseudo global exposure period to a rolling shutter period in the second direction relative to the pseudo global exposure period while increasing the pulse light emission intensity in a case where the controller is instructed to rapidly increase the exposure level in a state where the pulse light emission intensity has decreased from a predetermined maximum value.

4. The light source device
according to claim 1,
wherein the controller shifts a light emission component of a rolling shutter period in the first direction relative to the pseudo global exposure period to a rolling shutter period in the second direction relative to the pseudo global exposure period while decreasing the pulse light emission intensity in a case where the controller is instructed to rapidly decrease the exposure level.

5. The light source device
according to claim 4,
wherein the controller replaces the light emission component in the rolling shutter period in the second direction with increase in the pulse light emission intensity so that the pulse light emission intensity becomes a predetermined maximum value after the rolling shutter period in the second direction becomes equal to or greater than a predetermined period and an appropriate exposure level is reached by shift operation of the light emission component from the rolling shutter period in the first direction to the rolling shutter period in the second direction.

6. The light source device
according to claim 1,
wherein the controller further executes processing of correcting linearity of emitted light amount/current ratios of the plurality of semiconductor light emitting elements.

7. The light source device
according to claim 1,
wherein the controller executes offset light emission with pulsed light or continuous light in addition to light emission by the light emission profile.

* * * * *